United States Patent [19]
Bram et al.

[11] Patent Number: 5,969,102
[45] Date of Patent: Oct. 19, 1999

[54] LYMPHOCYTE SURFACE RECEPTOR THAT BINDS CAML, NUCLEIC ACIDS ENCODING THE SAME AND METHODS OF USE THEREOF

[75] Inventors: Richard J. Bram; Gotz Von Bulow, both of Memphis, Tenn.

[73] Assignee: St. Jude Children's Research Hospital, Memphis, Tenn.

[21] Appl. No.: 08/810,572

[22] Filed: Mar. 3, 1997

[51] Int. Cl.$^6$ .................................................. C07K 14/705
[52] U.S. Cl. ........................................... 530/350; 530/820
[58] Field of Search ........................... 530/350, 324–329, 530/820

[56] References Cited

U.S. PATENT DOCUMENTS 5,523,227  6/1996  Bram et al. .
5,541,291  7/1996  Keene .

FOREIGN PATENT DOCUMENTS

WO 95/35501  12/1995  WIPO .
WO 96/18641  6/1996  WIPO .

OTHER PUBLICATIONS

Birren et al. (1998) Sequence Database: AC003958.
Holloway et al. (1996) J. Biol. Chem. 271:8549–52.
Tashiro et al. (1993) Science 261:600–3.
von Bulow et al. (1997) Science 278:138–41.
von Bulow et al. (1997) Blood 90:246A–7.
Bairoch, Nucl. Acids Res., 21:3097–3103 (1993).
Bram & Crabtree, Nature, 371:355–358 (1994).
Bram et al., Mol. Cell. Biol., 13:4760–4769 (1993).
Clipstone and Crabtee, Nature, 357:695–7 (1992).
Crabtee & Clipstone, Annu. Rev. Biochem., 63:1045–1083 (1994).
Emmel et al., Science, 246:1617–1620 (1989).
Fiering et al., Genes Dev., 4:1823–1834 (1990).
Friedman & Weissman, Cell, 66:799–806 (1991).
Holloway & Bram, Biol. Chem., 271:8549–8552 (1996.
Hoth & Prenner, Physiol., 465:359–386 (1993).
Imboden et al., Immunol., 134:663–665 (1985).
Karttunen & Shastri, Proc. Natl. Acad. Sci. USA, 88:3972–3976 (1991).
Liu et al., Cell, 66:807–15 (1991).
O'Keefe et al., Nature, 357:629–4 (1992).
Premack et al., J. Immunol., 152:5226–5240 (1994).
Putney & Bird, Cell, 75:199–201 (1993).
Takebe, Y., et al., Mol. Cell. Biol., 8:466–472 (1988).
Truneh et al., Nature, 313:318–321 (1985).
Verweij et al., J. Biol. Chem., 265:15788–15795 (1990).
Weiss & Littman, Cell, 76:263–274 (1994).
Zweifach & Lewis, Proc. Natl. Acad. Sci. USA, 90:6295–6299 (1993).

*Primary Examiner*—David Saunders
*Assistant Examiner*—F. Pierre VanderVegt
*Attorney, Agent, or Firm*—Klauber & Jackson

[57] ABSTRACT

A novel lymphocyte receptor protein, its DNA sequence, and its role in the calcium activation pathway is described. The protein, or genetically engineered constructs encoding it, are shown to increase lymphocyte response, and to identify ligands of the protein receptor. Antibodies to the proteins of the invention are generated for diagnostic therapeutics. The protein and DNA can also be used for diagnostic purposes and for identifying agents for modulating the calcium induced activation pathway. A particular advantage of the present invention is that it provides lymphocyte activation of receptor found on all B cells, but only on a subset of T cells. The receptor can thus be targeted to specifically regulate B cell responses without affecting mature T cell activity. Such targeting specificity is always advantageous, particularly where an increase or decrease of antibody production is desired, e.g., during an infection (increase) or to avoid immune complex deposition complications (rheumatoid arthritis, glomerulonephritis, and other auto immune conditions).

24 Claims, 7 Drawing Sheets

Structure of TACI

MSGLGRSRRGGRSRVDQEERFPQGLWTGVAMRSCPEEQYW    40
DPLLGTCMSCKTICNHQSQRTCAAFCRSLSCRKEQGKFYD    80
HLLRDCISCASICGQHPKQCAYFCENKLRSPVNLPPELRR    120
QRSGEVENNSDNSGRYQGLEHRGSEASPALPGLKLSADQV    160
ALVYSTLGLCLCAVLCCFLVAVACFLKKRGDPCSCQPRSR    200
PRQSPAKSSQDHAMEAGSPVSTSPEPVETCSFCFPECRAP    240
TQESAVTPGTPDPTCAGRWGCHTRTTVLQPCPHIPDSGLG    280
IVCVPAQEGGPGA                               293

FIG.2A

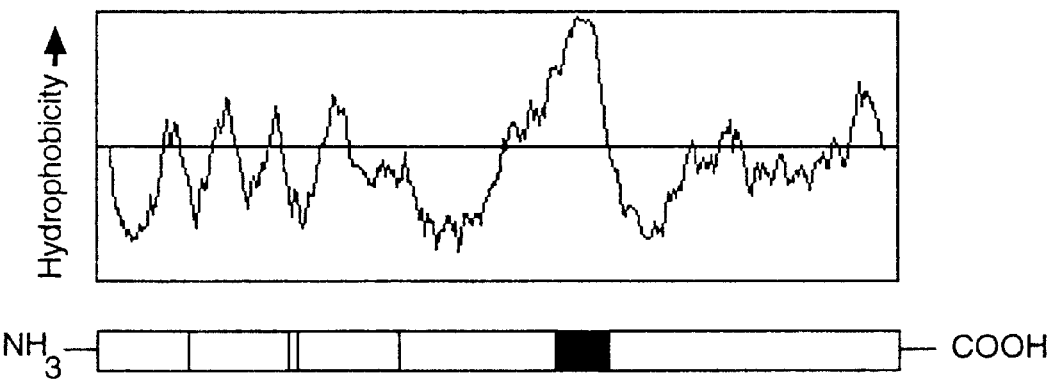

FIG.2B

The TNF Receptor Superfamily

TACI is a cell surface protein

TACI is a signaling protein resulting in activation of NF-AT-specific transcription

TACI interaction with CAML is critical for Ca²⁺ signaling

|  |  | pAS (Gal-4 DNA-binding domain) | | | |
| --- | --- | --- | --- | --- | --- |
|  |  | CAML (full length) | CAML (1-201) | CAML (202-296) | TACI (full length) |
| pACT (Gal-4 activation domain) | TACI (full length) | + | + | − | + |
|  | TACI (1-168) | − | − | − | ND |
|  | TACI (162-293) | + | + | − | ND |
|  | CAML (full length) | ND | ND | ND | + |

TACI interaction with CAML is critical for Ca$^{2+}$ signaling

5,969,102

LYMPHOCYTE SURFACE RECEPTOR THAT BINDS CAML, NUCLEIC ACIDS ENCODING THE SAME AND METHODS OF USE THEREOF

RESEARCH SUPPORT

The research leading to the present invention was supported in part by the Cancer Center CORE grant CA-21765 from the National Institutes of Health. The government may have certain rights in the present invention. Support for this invention was also provided by the AMERICAN LEBANESE SYRIAN ASSOCIATED CHARITIES, and American Cancer Society grant Bt-234, James McDonnell Foundation grant, JSMF 93-40-03.

FIELD OF THE INVENTION

The invention relates generally to the regulation of transcription in lymphocytes, proteins involved therein, antibodies thereof, nucleic acids that encode the proteins and uses of the nucleic acids, antibodies and proteins.

BACKGROUND OF THE INVENTION

Investigators are only beginning to unravel the mechanisms that control the cellular response to extrinsic factors. One basic feature of many of such mechanisms is the initial binding of an extrinsic factor, e.g., a ligand, to a cell surface membrane protein, i.e., a receptor. The binding of a ligand to its receptor usually effects a cellular change through a cascade of events. These events commonly involve other proteins, such as protein kinases, protein phosphatases, JAK proteins, Stat proteins, and/or G-proteins. In addition, there is generally a requirement for a transcription factor to bind to a specific DNA regulatory sequence in the nucleus of the cell, and thereby initiate the transcription of one or more particular genes.

Other factors are often involved. In antigen-stimulated lymphocyte activation, for example, calcium ($Ca^{2+}$) influx is also necessary for the ultimate initiation of DNA transcription. The increased cytoplasmic calcium concentration may originate as an external influx or a release of internal stores. Increased calcium concentration which activates the calcium-dependent protein phosphatase calcineurin acts in conjunction with other agents to signal the initiation of transcription. It is clear that the pathway involving calcium influx is essential to a number of processes involved with activation and proliferation of cells.

Intracellular calcium levels play a major function in a number of different cell types involving a number of different activities. In addition to the induction of gene transcription by calcium influx, many other calcium-dependent events, such as those which occur during muscle contraction (both cardiac and skeletal), vesicle degranulation (such as in the response of neutrophils and macrophages to infection, or basophil response to antigen stimulation, or release of acetylcholine by neurons), and closure of intracellular gap junctions offer opportunities for cellular regulation. The cell cycle can also involve fluxes of calcium. Intracellular chelators which block changes in intracellular calcium concentration can block the cell cycle from progressing, thereby arresting cell division. [Rabinovich et al., *J. of Immunol.*, 137:952–961 (1986)]. Therefore, regulation of calcium can be effective in modulating cell division in normal and diseased cells.

Lymphocytes are a primary component of the cellular arm of the immune system. Activation of one particular type of lymphocyte, a T-cell, can result through the stimulation of a T-cell receptor by e.g., the binding of a T-cell receptor (TCR) to an antigen presented by an antigen-presenting cell. This stimulation results in the activation a $Ca^{2+}$-dependent phosphatase, calcineurin. Activated calcineurin, in turn, activates NF-AT, a lymphocyte specific transcription factor that together with a companion transcription factor, AP-1, effects the expression of the inducible T-cell growth factor, interleukin-2 (IL-2). Activation of AP-1 is a calcium-independent process that involves protein kinase C, and can be experimentally achieved with the addition of phorbol myristate acetate (PMA). The immunosuppressant drug cyclosporin A (CsA) binds to and inhibits the prolyl isomerase activity of cyclophilin and the resulting drug-isomerase complex inactivates calcineurin, by a direct interaction near the active site of the enzyme. [Liu et al., *Cell*, 66:807–15 (1991)]; [Clipstone and Crabtree, *Nature*, 357:695–7 (1992)]; [O'Keefe et al., *Nature*, 357:692–4 (1992)]. NF-KB is a third key transcription factor which is important in the activation of lymphocytes and which is activated following the stimulation of the T-cell or B-cell antigen receptor.

Another protein associated with the calcium signaling pathway in lymphocytes is the recently identified calcium-signal modulating cyclophilin ligand (CAML) [Bram, R. J. and Crabtree, G. R., DNA Encoding Calcium-Signal Modulating Cyclophilin Ligand, U.S. Pat. No. 5,523,227, Issued Jun. 4, 1996, hereby incorporated by reference in its entirety]. CAML binds cyclophilin B with reasonable specificity, i.e., CAML does not bind cyclophilin A or C. Unlike the cyclosporin A-cyclophilin complex, however, the CAML-cyclophilin B complex does not directly bind to calcineurin. Thus CAML appears to affect calcineurin through its regulation of $Ca^{2+}$ influx. As expected, CsA can indirectly block the activating effect of CAML on transcription, by inhibiting calcineurin. In addition, CAML appears to have no effect on the activation of AP-1, and so the CAML-dependent activation of NF-AT experimentally requires the addition of PMA.

CAML acts downstream from an extrinsic signal but upstream from calcineurin. The location of CAML in cytoplasmic vesicles suggests that it can regulate $Ca^{2+}$ influx by modulating intracellular $Ca^{2+}$ release. However, there remains a need to determine the natural factor (or factors) that communicate the external signal to the cellular CAML. Further, there is a need to understand how CAML interacts with this factor in order to learn how to better control the important cellular processes that CAML helps to regulate. A different class of signaling molecule is the TNFR family of cell surface receptors [Smith et al., *Cell* 76:959–62 (1994)]. These receptors initiate intracellular signals leading to the onset of cell growth, death, or gain of effector function.

SUMMARY OF THE INVENTION

A novel lymphocyte receptor, its DNA sequence, and its role in the calcium activation pathway is described. The protein, or genetically engineered constructs encoding it, can be used to enhance lymphocyte response, or to identify ligands of the protein receptor. The soluble, extracellular domain can be used to inhibit cellular activation. Antibodies to the protein can be generated for diagnostic or therapeutic uses. The protein and DNA may also be used for diagnostic purposes and for identifying agents for modulating the calcium induced activation pathway. Knowledge of the coding sequence allows for manipulation of cells to elucidate the mechanism of which CAML is a part.

A particular advantage of the present invention is that it provides lymphocyte activation of a receptor found on all B cells, but only on a subset of T cells. The receptor can thus be targeted to specifically regulate B cell responses without affecting mature T cell activity. Such targeting specificity is always advantageous, particularly where an increase or decrease of antibody production independent of cellular immune responses is desired, e.g., during an infection (increase) or to avoid immune complex deposition complications (rheumatoid arthritis, glomerulonephritis, and other autoimmune conditions).

Crosslinking the novel cell surface receptor of the present invention activates B cells and some populations of T cells. Activation of these cells increases the immune system activity. On the other hand, blocking or inhibiting the novel cell surface receptor of the present invention can result in immunosuppression. Depending on the endogenous level of activation of the receptor, which can be evaluated using the antibodies or nucleic acids of the invention, receptor activity can be enhanced or suppressed to achieve a desired outcome. Either activating or inhibiting the function of the novel cell surface receptor of the present invention can be used to treat cancers of T and B cells.

The present invention includes an isolated Transmembrane Activator and CAML-Interactor (TACI) protein that functions as a cell surface signaling protein and comprises an extracellular domain, a membrane spanning segment, and a cytoplasmic domain. In one embodiment, the TACI protein is a plasma membrane receptor in which the extracellular domain resides at the N-terminal portion of the protein and the cytoplasmic domain resides at the C-terminal portion of the protein. The N-terminal portion of the TACI protein functions as a binding site for a ligand that stimulates the activation of the cell by inducing the binding of the C-terminal portion of the TACI protein to the N-terminal domain of CAML. Since CAML is an integral membrane protein that is localized to cytoplasmic vesicles, the TACI protein is a plasma membrane receptor that directly interacts with an intracellular organelle in lymphocytes.

In one embodiment, the monomeric form of the isolated TACI protein consists of about 295 amino acids. In a preferred embodiment the monomeric form of a Transmembrane Activator and CAML Interactor (TACI) protein contains 280 to 310 amino acids. In more preferred embodiments the monomeric form of a TACI protein contains 290 to 296 amino acids. In a specific embodiment exemplified infra, the monomeric form of a TACI protein contains 293 amino acids.

One embodiment of the isolated TACI protein contains two TNFR superfamily cysteine-rich repeats [Bairoch, *Nucl. Acids Res.*, 21:3097–3103 (1993)]. In a preferred embodiment, a TACI protein that is appropriately stimulated, in situ, such as by a ligand or an anti-TACI antibody, initiates the activation of a transcription factor through the combination of a $Ca^{2+}$-dependent pathway and a $Ca^{2+}$-independent pathway.

The present invention includes an isolated nucleic acid that consists of at least 18 nucleotides of a nucleotide sequence that has at least 60% similarity with SEQ ID NO:1, or alternatively at least 60% similarity with the coding sequence of SEQ ID NO:1. The nucleotide sequence encodes a TACI protein which has a binding affinity for CAML. In one such embodiment the isolated nucleic acid encodes a TACI protein.

In a preferred embodiment of the present invention the nucleotide sequence has at least 75% similarity with SEQ ID NO:1, or has at least 75% similarity with the coding sequence of SEQ ID NO:1. In a more preferred embodiment, the nucleotide sequence has at least 90% similarity with SEQ ID NO:1, or has at least 90% similarity with the coding sequence of SEQ ID NO:1. In an even more preferred embodiment, the nucleotide sequence has between 95–98% similarity with SEQ ID NO:1, or has between 95–98% similarity with the coding sequence of SEQ ID NO:1. In a particular embodiment the nucleotide sequence is SEQ ID NO.1. In a related embodiment, the nucleotide sequence consists of the coding sequence of SEQ ID NO:1. In a specific embodiment, exemplified infra, the isolated nucleic acid has the nucleotide sequence of SEQ ID NO:1. In a related embodiment, the isolated nucleic acid consists of the coding sequence of SEQ ID NO:1.

In another related embodiment the present invention includes an isolated nucleic acid which contains at least 18 nucleotides and hybridizes to SEQ ID NO:1, or more particularly hybridizes to the coding sequence of SEQ ID NO:1. In one such embodiment, the hybridization is performed under moderate stringency. In another embodiment, the hybridization is performed under standard hybridization conditions. In yet a third embodiment, the hybridization is performed under stringent hybridization conditions.

In still another related embodiment the present invention includes an isolated nucleic acid which contains at least 18 nucleotides of a nucleotide sequence that encodes a TACI protein having an amino acid sequence of either SEQ ID NO:2, or SEQ ID NO:2 with one or more conservative substitutions. In one such embodiments of this type, the isolated nucleic acid encodes an N-terminal fragment of the TACI protein corresponding to the extracellular domain. In another embodiment, the isolated nucleic acid encodes a C-terminal fragment of the TACI protein that is sufficient to bind to the N-terminal 146 amino acids of CAML. In yet another embodiment, the isolated nucleic acid encodes the transmembrane portion of the TACI protein. In still another embodiment, the isolated nucleic acid encodes the full-length TACI protein.

In a preferred embodiment of the present invention, the isolated nucleic acid consists of at least 24 nucleotides. In a more preferred embodiment, the isolated nucleic acid consists of at least 30 nucleotides. In an even more preferred embodiment, the isolated nucleic acid consists of at least 36 nucleotides. Oligonucleotides of the invention can be used as nucleic acid probes, PCR primers, antisense nucleic acids, and the like, for diagnostic and therapeutic purposes.

In one embodiment of the present invention, an isolated nucleic acid encodes a C-terminal fragment of the TACI protein that is sufficient to bind to the N-terminal 146 amino acids of CAML. In one particular embodiment of this type, the C-terminal fragment contains about 126 amino acids. In another embodiment of this type the C-terminal fragment has an amino acid sequence of either SEQ ID NO:4, or SEQ ID NO:4 with one or more conservative substitutions.

In another embodiment, the isolated nucleic acid encodes an N-terminal fragment of the CAML-binding protein corresponding to the extracellular domain. In a particular embodiment of this type the N-terminal fragment has an amino acid sequence of either SEQ ID NO:6, or SEQ ID NO:6 with one or more conservative substitutions.

In a preferred embodiment, the isolated nucleic acid encodes a TACI protein that has a binding affinity for CAML. When such a TACI protein is appropriately stimulated, in situ, it initiates activation of a transcription factor through the combination of a $Ca^{2+}$-dependent pathway and a $Ca^{2+}$-independent pathway. In a more preferred embodiment, the isolated nucleic acid encodes a TACI protein having the amino acid sequence of SEQ ID NO:2.

The present invention also includes a DNA construct comprising an isolated nucleic acid of the present invention that is a recombinant DNA operatively linked to an expression control sequence. The expression control sequence can be selected from the group consisting of the early or late promoters of SV40 or adenovirus, the lac system, the trp system, the TAC system, the TRC system, the major operator and promoter regions of phage λ, the control regions of fd coat protein, the promoter for 3-phosphoglycerate kinase, the promoters of acid phosphatase and the promoters of the yeast α-mating factors.

In a preferred embodiment, the expression control sequence is either a standard tet inducible promoter, a metallothionein promoter, or an ecdysone promoter. In a more preferred embodiment, the expression control sequence is the $SR_\alpha$ promoter.

The present invention also includes a unicellular host transformed with a recombinant DNA construct of the present invention. In one embodiment the unicellular host is a prokaryote. In another embodiment the unicellular host is a eukaryote. Preferably the eukaryotic host is a mammalian cell, for example, a COS, CHO or Jurkat T cell, which could be useful for evaluating activity of the TACI protein or to identify modulatory agents.

The present invention includes the isolated polypeptides encoded by the nucleic acids of the present invention, fragments thereof, and fusion proteins thereof. In one embodiment, the polypeptide fragment consists of an N-terminal fragment of the TACI protein corresponding to the regulatory extracellular domain. In a particular embodiment the N-terminal fragment has an amino acid sequence of SEQ ID NO:6 or SEQ ID NO:6 with one or more conservative substitutions.

In another embodiment, the polypeptide fragment consists of a C-terminal fragment of the TACI protein that is sufficient to bind to the N-terminal 146 amino acids of CAML. In one such embodiment, the C-terminal fragment contains 95 to 130 amino acids. In a specific embodiment, the C-terminal fragment contains the C-terminal 126 amino acids of SEQ ID NO:2. In an alternative embodiment the C-terminal fragment of the TACI protein contains about 110 amino acids. In a preferred embodiment of this type, the C-terminal fragment contains 107 amino acids and has an amino acid sequence of SEQ ID NO:4.

The present invention also includes the preparation of a recombinant form of the extracellular portion of a TACI protein, thereby creating a dominant-negative or blocking reagent. This component intercepts the normal endogenous ligands which serve to crosslink and activate the TACI protein. Administration of such a polypeptide acts to suppress the immune system. Such administration is useful in the treatment or prevention of autoimmune disease or graft-rejection or graft-vs-host disease following transplantation.

A chimeric TACI protein of the invention may be a protein that is generated by joining the extracellular domain of another receptor molecule with a transmembrane domain and the intracellular domain of a TACI protein. In another embodiment, the extracellular domain of a TACI protein can be joined with a transmembrane domain and an intracellular domain of another receptor molecule. The transmembrane domain can be the transmembrane domain of a TACI protein, the transmembrane domain of the other receptor, or a different transmembrane domain. Preferably, the transmembrane domain is from the same protein component of the chimera as the extracellular domain.

In a preferred embodiment the polypeptide is a TACI protein encoded by a nucleic acid of the present invention that has a binding affinity for CAML and when appropriately stimulated, in situ, initiates activation of a transcription factor through the combination of a $Ca^{2+}$-dependent pathway and a $Ca^{2+}$-independent pathway.

The present invention also includes antisense nucleic acids that hybridize under physiological conditions to the mRNAs that encode the TACI proteins of the present invention. Such antisense nucleic acids may be RNA transcribed from an antisense gene, or RNA or DNA produced exogenously (whether by expression or chemical synthesis). Preferably, a synthetic antisense nucleic acid is prepared with non-naturally occurring bonds to prevent its rapid hydrolysis and thus increase its effective half-life.

A knockout animal is also part of the present invention. The knockout animal comprises a first and second allele which each naturally encode and express functional TACI protein but in which at least one of the two alleles is defective and thereby prevents the animal from expressing an adequate amount of the TACI protein. In one embodiment of this type, the first allele contains a defect that prevents the animal from expressing any functional TACI protein. In a preferred embodiment, a knockout animal contains both a defective first allele and a defective second allele. These defective alleles prevent the animal from expressing functional TACI protein. In a preferred embodiment, the knockout animal is a knockout mouse.

The present invention also includes antibodies to all of the nucleic acids and polypeptides of the present invention. In a specific embodiment, the antibody is prepared against the TACI protein having an amino acid sequence of SEQ ID NO:2, or an antigenic fragment thereof. The antibodies of the present invention can be either monoclonal antibodies or polyclonal antibodies. In one embodiment, the antibody is a monoclonal antibody that is a chimeric antibody.

An immortal cell line that produces a monoclonal antibody of the present invention is also part of the present invention. In a specific embodiment of this immortal cell line, the monoclonal antibody is prepared against the TACI protein having an amino acid sequence of SEQ ID NO:2 or an antigenic fragment thereof.

The present invention also includes an N-terminal fragment of CAML that is sufficient to bind to the C-terminal 126 amino acid fragment of TACI-1. In one such embodiment, the N-terminal fragment of CAML contains 146 amino acids. This N-terminal fragment of CAML can serve as an inhibitor of TACI-CAML binding.

The present invention includes methods of making TACI proteins, fragments thereof and fusion proteins thereof. In one embodiment the method comprises introducing an expression vector comprising a nucleic acid encoding a polypeptide that is a TACI protein, or a fragment thereof, or a fusion protein thereof, into a host cell and expressing the encoded polypeptide. In a preferred embodiment the expressed polypeptide has a binding affinity for CAML. In a more preferred embodiment the polypeptide, when appropriately stimulated, in situ, initiates activation of a transcription factor through the combination of a $Ca^{2+}$-dependent and a $Ca^{2+}$-independent pathway. In the most preferred embodiment of this type the expressed polypeptide is a TACI protein having an amino acid sequence of SEQ ID NO:2.

Methods of purifying the expressed polypeptides encoding TACI proteins, fragments thereof and fusion proteins thereof, are also part of the present invention, as are the purified expressed polypeptides themselves.

The present invention also includes methods for identifying a ligand for a TACI protein. One embodiment of such a method comprises contacting the N-terminal extracellular polypeptide of a TACI protein with a candidate molecule and detecting the binding of the N-terminal extracellular polypeptide with the candidate molecule. The binding of the N-terminal extracellular polypeptide with the candidate molecule indicates that the candidate molecule is ligand.

In an alternative method for identifying a ligand for a TACI protein, a functional TACI protein is used. In preferred embodiments of this type the functional TACI protein is TACI-1. The binding of the functional TACI protein with the candidate molecule indicates that the candidate molecule is a ligand. In one such embodiment, binding of the candidate molecule to the functional TACI protein is determined by detecting cellular activation as a function of the level of activation of the AP-1 pathway. In another embodiment, binding of the candidate molecule to the functional TACI protein is determined by detecting cellular activation as a function of the level of activation of the CAML pathway.

In another embodiment, binding of the candidate molecule to the functional TACI protein is determined by detecting cellular activation as a function of the level of the concentration of the NF-AT transcription factor. In still another embodiment, binding of the candidate molecule to the functional TACI protein is determined by detecting cellular activation as a function of the level of activation of the NF-KB pathway. In yet another embodiment, binding of the candidate molecule to the functional TACI protein is determined by detecting cellular activation as a function of the level of the activation of NF-AT. In this case, the level of activation of NF-AT can be determined by methods including demonstrating cytoplasm to nuclear translocation of NF-AT; the relative dephosphorylation of NF-AT; and/or by NF-AT-dependent transcription.

In preferred embodiments, more than one of the above determinations of cellular activation is made, and the candidate molecule is identified as a ligand when all the determinations made indicate the binding of the candidate molecule to the TACI protein. In the most preferred embodiment, all of the above determinations of cellular activation are made and the candidate molecule is identified as a ligand when all of these determinations indicate that the candidate molecule binds to the TACI protein.

Methods for identifying a ligand for a TACI protein may be performed in a large number of expression systems in the TACI protein can be expressed. One embodiment employs the use of a yeast two-hybrid expression system using the TACI protein as "bait." In another embodiment, interaction cloning from *E. coli* expression-libraries may be employed. In yet another embodiment, functional expression cloning in mammalian cells of the TACI protein can be utilized. In a preferred embodiment, the mammalian cells are B-cell derived lines such as Burkitt's Lymphoma, EBV-immortalized cell lines, or multiple myeloma cell lines. In a more preferred embodiment of this type, the TACI protein is expressed in Jurkat T cells containing a reporter gene under control of an NF-AT promoter. In one such embodiment, the reporter gene encodes secreted alkaline phosphatase (SEAP) as the marker.

The present invention also includes methods of screening for an immunosuppressant drug that inhibits the activation of B cells to a greater extent than it inhibits the activation of mature T cells. In preferred embodiments of this type, the immunosuppressant drug inhibits the activation of B cells, but does not inhibit the activation of mature T cells. Such methods may be performed in transformed T cells, such as a Jurkat T cell, which can be genetically manipulated to express the TACI protein; or in B cells that naturally express the TACI protein. The present invention also includes the immunosuppressant drugs identified which inhibit the activation of B cells, but not the activation of mature T cells.

The present invention includes methods of identifying an immunosuppressant drug that selectively blocks the action of B lymphocytes without effecting mature T lymphocytes. One such embodiment comprises contacting a first lymphocyte with a potential drug, wherein the first lymphocyte contains a TACI protein and a first marker protein. The first marker protein is transcribed when the TACI protein is stimulated in the absence of a candidate drug. The TACI protein is stimulated, and the first marker protein is detected under conditions in which if it is transcribed, it is detectable. A potential drug is selected as a candidate drug when the first marker protein cannot be detected. Next, a second lymphocyte is contacted with the candidate drug, wherein the second lymphocyte contains a T cell receptor, and a second marker protein that is transcribed when the T cell receptor is stimulated either in the absence or the presence of the immunosuppressant drug. The T cell receptor is stimulated and the second marker protein is detected under conditions in which if it is transcribed, it is detectable. A candidate drug is identified as an immunosuppressant drug when the second marker protein is detected, since the immunosuppressant drug interferes with the pathway (or aspect thereof) involving the TACI protein but not the pathway (or aspect thereof) involving the T cell receptor.

In one embodiment, the first and second lymphocytes are Jurkat T cells that have been modified to express a TACI protein. In one such particular embodiment the method comprises contacting a first Jurkat T cell with a potential drug, wherein the first Jurkat T cell has been genetically engineered to express a TACI protein and a first reporter gene. The first reporter gene is controlled by an NF-AT promoter, and encodes a first marker protein. The TACI protein is activated, and the amount of expression of the first marker protein is quantified. A potential drug is selected as a candidate drug when the amount of the first marker protein expressed in the presence of the candidate drug is decreased relative to the amount expressed in the absence of the candidate drug. The candidate drug is then contacted with a second Jurkat T cell that contains a T cell receptor and a second reporter gene. The second reporter gene is controlled by an NF-AT promoter, and encodes a second marker protein. The T cell receptor is activated and the amount of expression of the second marker protein is quantified and then compared to the amount of second marker protein expressed in the absence of the candidate drug. A candidate drug is identified as an immunosuppressant drug if either there is no decrease in the amount of expression of the second marker protein in the presence of the candidate drug, or the decrease in the expression of the second marker protein is measurably less than the corresponding decrease in expression of the first marker protein in the presence of the candidate drug.

Any of the marker proteins described herein may be used for this aspect of the invention including SEAP, LacZ or luciferase. The first and second marker protein can be the same protein or two different proteins. The TACI protein may be activated with an antibody raised against a TACI protein, or an active fragment thereof, or a fusion protein thereof. In a preferred embodiment, the TACI protein is TACI-1. Several promoters can be used to control the reporter gene including the NF-AT promoter mentioned above and the AP-1 promoter. Potential drugs can be obtained from any of the drug libraries currently available, and from the chemical and phage libraries described herein.

These and other aspects of the present invention will be better appreciated by reference to the following drawings and Detailed Description.

BRIEF DESCRIPTION OF THE DRAWINGS

FIG. 1 depicts a Northern blot of the tissues indicated probed with TACI-1 cDNA. Other tissues probed include the heart, brain, placenta, lung, liver, skeletal muscle, kidney and the pancreas, none of which showed any TACI-1 mRNA expression.

FIG. 2a depicts the amino acid sequence of TACI-1. The proposed transmembrane domain is shown in boxed print and the Prosite TNFR_NGFR motifs are underlined.

FIG. 2b depicts a Kyte-Doolittle hydrophobicity plot and schematic diagram of TACI-1 showing the positions of the putative transmembrane domain (solid black) and the TNFR_NGFR motifs (stippled).

FIG. 3. TACI-1 is a cell surface protein.

FIG. 4. TACI-1 is a signaling protein that functions in the activation of NF-AT-specific transcription.

FIG. 5. TACI-1 interaction with CAML is critical for $Ca^{2+}$ signaling.

DETAILED DESCRIPTION OF THE INVENTION

Figure 1:
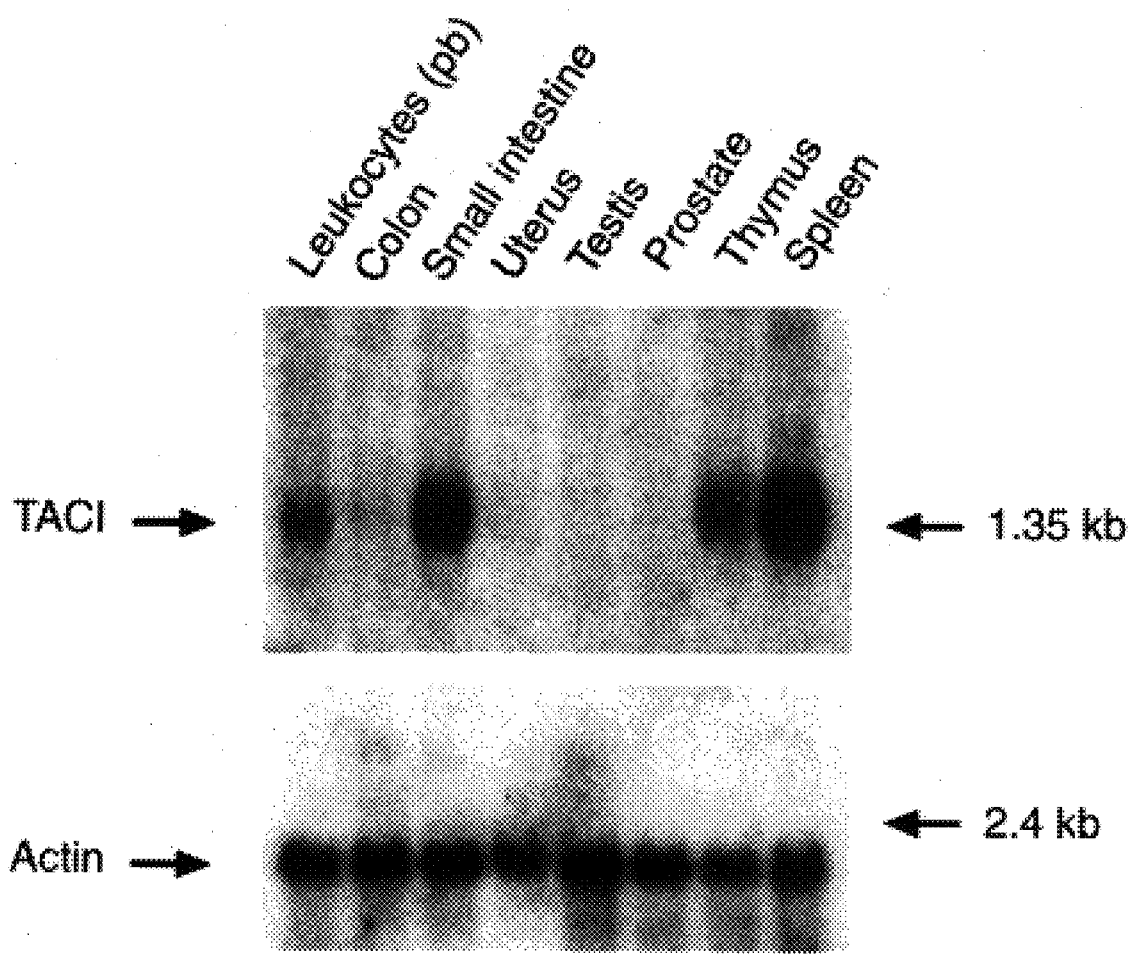
FIG. 1. The tissue distribution, protein sequence and other salient features of TACI-1.

The present invention, in its broadest aspect, provides a novel cell surface receptor that is normally present in B-lymphocytes, and to a much lesser extent in immature T-lymphocytes. The role of the cell surface receptor, the Transmembrane Activator and CAML-Interactor (TACI) protein, is to participate in alternate or co-stimulatory pathways to activate or control lymphocyte function. These functions can include response of lymphocytes to foreign antigens in infection, or to cancer, in the graft-rejection, and graft-vs-host reaction. Additionally, activation of lymphocyte signaling plays a key role during lymphocyte development, thus allowing the positive selection of functional lymphocytes and negative selection against self-reactive clones. When activated, the TACI protein stimulates the influx of calcium in lymphocytes. Such calcium influx can, under specific circumstances, lead to the onset of programmed cell death (apoptosis).

The terms "Transmembrane Activator and CAML-Interactor" protein or "TACI" or "TACI protein" are used herein interchangeably with "transmembrane CAML-binding protein" or "TCB" or "TCB protein" and refer to proteinaceous material including single or multiple proteins that act as a novel cell surface receptor that is normally present in B-lymphocytes. This cell surface receptor has the profile of activities set forth herein. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the protein. Included within the scope of these terms are proteins specifically recited herein, as well as all substantially homologous analogs and allelic variations.

In one embodiment the Transmembrane Activator and CAML-Interactor is TACI-1, the human homologue. As shown in the Example, infra, TACI-1 initiates a previously undetected signal transduction mechanism that directly links cell surface stimuli to the intracellular signaling molecule, CAML. TACI-1 therefore is a member of a new class of lymphocyte-specific cell surface receptors that modulate the immune response and thus may be used as tool to regulate the immune system in either a positive or a negative direction. In a specific embodiment, TACI-1 has the amino acid sequence set forth in SEQ ID NO:2.

As used herein when a particular nucleic acid is said to encode a protein or polypeptide of the present invention, it is meant that the portion of the particular nucleic acid that consists of the coding sequence for that protein or polypeptide is being identified. For example, the coding region of SEQ ID NO:1 is from nucleotide 14 to nucleotide 895, including the 3 nucleotide translation stop codon at the 3/terminus.

For many purposes, there is a substantial interest in being able to selectively prevent activation of lymphocytes or in the alternative to selectively enhance their activation. For example, for lymphocyte mediated autoimmune diseases, transplant rejection syndrome, and graft-versus host disease, inhibiting the activation of the lymphocyte involved is a viable or necessary treatment for the disease. Furthermore, in the case of myelomas, lymphomas, and leukemias, especially of B cells or immature T cells, there is an interest in slowing the proliferation of cancer cells, which may allow for therapies which are not as destructive to the host as present day therapies. On the other hand, for infections or anti-tumor immune responses, there would be interest in being able to activate lymphocytes to more rapidly respond to the pathogen. Thus, the present invention enables selection of useful agents, e.g., synthetic organic compounds which can activate and/or deactivate lymphocytes by providing a previously unknown key component in the lymphocyte activation pathway.

In addition, as one understands the activation pathway more completely, one is able to modulate the pathway more effectively, such as providing for agents which are selective for a particular set or subset of a cellular population. Since in many cases activation requires co-stimulation, being able to manipulate agents available to the cell may allow for such cellular activity. In this context, the identification of a target protein that can be used to develop drugs that modulate a particular pathway, such as the CAML-mediated activation pathway, would allow physicians to particularly treat distinct immune conditions without over-stimulating or over-suppressing other delicate aspects of the immune system that are otherwise functioning well. Such targeted stimulation can be used to specifically amplify the effects of immune stimulators, such as IL-2, thus allowing for the use of lower doses of the immune stimulator and reducing side effects.

Furthermore, the invention is an important advance in understanding the CAML-mediated activation pathway, by permitting selective evaluation and control over the presence or the absence of a particular intermediate in that pathway. This can be achieved with a knock-out animal using homologous recombination, integration of genes providing for antisense sequences, introduction of expression constructs involving inducible promoters, and the like. There is also an interest in being able to determine when a particular gene is being expressed or is silent, the nature of the cells in which the protein is expressed, and the like. Therefore, there is substantial interest in identifying specific components of cellular pathways to allow for understanding an activation pathway, selectively modulating that pathway, and developing drugs which may be active in binding to the target protein. In this way, drugs can be screened to inhibit such specific pathways.

One particular aspect of the present invention includes a drug screen that uses TACI as a tool for developing immunosuppressant drugs specific for B-lymphocytes. Such immunosuppressant drugs would selectively block the action of B-lymphocytes, while leaving T-cells intact to protect patients from viral pathogens. These drugs would be useful in treating diseases such as Systemic Lupus Erythematosus, a disease due to an over-activation of the B-lymphocyte response, or multiple myeloma (e.g., Bence-Jones Myeloma).

Cross-linking the TACI protein activates calcium influx and potentially other secondary messengers. Its mode of action can be mediated by CAML. Unlike known cell surface signaling molecules that are specific for B cells or T cells, such as CD4, CD8, TCR, and CD3, the novel cell surface receptor of the present invention physically interacts with CAML. In addition, there is no sequence homology between the novel cell surface receptor of the present invention and any of these known lymphocyte cell surface signaling molecules, or any other cell surface signaling molecules.

TACI Proteins and Polypeptides

In a broad embodiment, the present invention provides TACI proteins. Such proteins include an extracellular domain, a transmembrane domain, and a cytoplasmic domain. The extracellular domain binds ligand. Upon ligand binding, the cytoplasmic domain binds CAML, thus initiating a $Ca^{2+}$-dependent activation pathway. Receptor oligomerization, e.g., by binding ligand or with an anti-receptor antibody, also initiates a non-$Ca^{2+}$-dependent activation pathway.

The monomeric form of a TACI protein contains about 295 amino acids. As used herein "about 295 amino acids" means between 265 to 325 amino acids, i.e., roughly plus or minus 10%.

The invention further relates to functionally active polypeptide components of TACI. In one aspect, a functionally active component of TACI is an antigenic fragment, e.g., a peptide reactive with anti-TACI antibodies, or which, when conjugated to a carrier, can be used to generate anti-TACI antibodies. Another functionally active fragment includes the extracellular domain, which binds ligand. The extracellular domain corresponds to the N-terminal fragment of TACI, e.g., from the first amino acid residue of mature TACI to the transmembrane domain. In a specific embodiment, the extracellular domain has the amino acid sequence corresponding to about residue 1 to about residue 166 of SEQ ID NO:6. The ligand-binding region of TACI is a sub-fragment of the N-terminal fragment corresponding to the extracellular domain.

Still another functionally active fragment is the cytoplasmic domain, e.g., from the C-terminal end of the transmembrane domain to the C-terminus of TACI. The cytoplasmic domain of TACI mediates signal transduction via $Ca^{2+}$-dependent and $Ca^{2+}$-independent mechanisms.

The cytoplasmic domain includes the CAML-binding region of TACI. In particular, this domain binds a polypeptide corresponding to the N-terminal 146 amino acid residues of CAML. In a specific embodiment, the cytoplasmic domain corresponds to from about amino acid residue 187 to about amino acid residue 293 of SEQ ID NO:2.

In yet another embodiment, the present invention provides proteolytic fragments of a TACI protein. Such fragments can be prepared by enzymatic digestion, e.g., with Saureus Polypeptides V8 in papain trypsin, chymotrypsin, cathepsin, collagenase, enteropeptidase, thrombin, or fibrinolytic or clotting enzymes; by chemical cleavage, e.g., with cyanogen bromide, or sodium borohydride; etc.

In a specific embodiment, the TACI protein is a receptor protein having the amino acid sequence as shown in SEQ ID NO:2, from residue 1 to residue 293. The present invention contemplates allelic variants of TACI, homologous TACI proteins from other species, and TACI analogs, e.g., prepared by making conservative amino acid substitutions, whether by genetic engineering or by chemical synthesis. A TACI analogue of the invention also includes TACI antigenic fragments that contain, e.g., a terminal cysteine residue to facilitate cross-linking to a carrier protein.

There are no reported DNA sequences that are closely related to that for TACI-1. A search for Prosite motifs in TACI-1 reveals one TNFR_NGFR pattern, which consists of C-x(4,6)-[FYH]-x(5,10)-C-x(0,2)-C-x(2,3)-C-x(7,11)-C-x(4,6)-[DNEQSKP]SEQ ID NO:11-x(2)-C in the N-terminal half of the protein (where e.g., C-x(4,6)-[FYH] is indicative of an amino acid sequence starting with cysteine followed by either 4, 5, or 6 unspecified amino acids, further followed by either a phenylalanine, a tyrosine, or a histidine). This motif is found in a number of proteins, most of which are receptors for growth factors. Some of these proteins have one copy of this motif. A comparison of the TACI-1 protein sequence with itself reveals a significant repeat between the TNFR_NGFR motif at residues 33–66 and residues 70–104. This analysis drew attention to the presence of two TNFR-type cysteine-rich domains encompassing these regions that indicate that TACI-1 is a member of the superfamily of TNFR receptors.

Synthetic TAClpolypeptides. The term "polypeptide" is used in its broadest sense to refer to a compound of two or more subunit amino acids, amino acid analogs, or peptidomimetics.

The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein. According to the invention, TACI fragments, such as antigenic fragments, or potentially even full-length TACI, can be prepared synthetically.

Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^{\alpha}$-amino protected $N^{\alpha}$-t-butyloxycarbonyl) amino acid resin with the standard de-protecting, neutralization, coupling and wash protocols of the original solid phase procedure of Merrifield [*J. Am. Chem. Soc.*, 85:2149–2154 (1963)], or the base-labile $N^{\alpha}$-amino protected 9-fluorenylmethoxycarbonyl (Fmoc) amino acids first described by Carpino and Han [*J. Org. Chem.*, 37:3403–3409 (1972)]. Both Fmoc and Boc $N^{\alpha}$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^{\alpha}$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity [Hruby, *Life Sciences*, 31:189–199 (1982)]; [Hruby et al., *Biochem J.*, 268:249–262 (1990)]; the present invention provides a method to produce a constrained peptide that incorporates random sequences at all other positions.

Non-classical Amino Acids that Induce Conformational Constraints

The following non-classical amino acids may be incorporated in the peptide in order to introduce particular conformational motifs: 1,2,3,4-tetrahydroisoquinoline-3-carboxylate [Kazmierski et al., *J. Am. Chem. Soc.*, 113:2275–2283 (1991)]; (2S,3S)-methyl-phenylalanine, (2S,3R)-methyl-phenylalanine, (2R,3S)-methyl-phenylalanine and (2R,3R)-methyl-phenylalanine [Kazmierski and Hruby, *Tetrahedron Lett.*, (1991)]; 2-aminotetrahydronaphthalene-2-carboxylic acid [Landis, Ph. D. Thesis, University of Arizona, (1989)]; hydroxy-1,2,3,4-tetrahydroisoquinoline-3-carboxylate [Miyake etal., *J. Takeda Res. Labs.*, 43:53–76 (1989)]; β-carboline (D and L) [Kazmierski, Ph. D. Thesis, University of Arizona, (1988)]; HIC (histidine isoquinoline carboxylic acid) [Zechel et al., *Int. J. Pep. Protein Res.*, 43 (1991)]; and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., *J. Org. Chem.*, 50:5834–5838 (1985)]; β-sheet inducing analogs [Kemp et al., *Tetrahedron Lett.*, 29:5081–5082 (1988)]; β-turn inducing analogs [Kemp et al., *Tetrahedron Lett.*, 29:5057–5060 (1988)]; -helix inducing analogs [Kemp et al., *Tetrahedron Lett.*, 29:4935–4938 (1988)]; γ-turn inducing analogs [Kemp etal., *J. Org. Chem.*, 54:109:115 (1989)]; and analogs provided by the following references: Nagai and Sato, *Tetrahedron Lett.*, 26:647–650 (1985); DiMaio et al., *J. Chem. Soc. Perkin Trans., p.* 1687 (1989); also a Gly-Ala turn analog [Kahn et al., *Tetrahedron Lett.*, 30:2317 (1989)]; amide bond isostere [Jones et al., *Tetrahedron Lett.*, 29:3853–3856 (1988)]; tretrazol [Zabrocki et al., *J. Am. Chem. Soc.*, 110:5875–5880 (1988)]; DTC [Samanen et al., *Int. J. Protein Pep. Res.*, 35:501:509 (1990)]; and analogs taught in Olson et al., *J. Am. Chem. Sci.*, 112:323–333 (1990) and Garvey et al., *J. Org. Chem.*, 56:436 (1990). Conformationally restricted mimetics of beta turns and beta bulges, and peptides containing them, are described in U.S. Pat. No. 5,440,013, issued Aug. 8, 1995 to Kahn.

Protein derivatives. There are two major classes of peptide-carbohydrate linkages to proteins. First, ether bonds join the serine or threonine hydroxyl to a hydroxyl of the sugar. Second, amide bonds join glutamate or aspartate carboxyl groups to an amino group on the sugar. Acetal and ketal bonds may also bind carbohydrate to peptide.

Generally, the TACI protein, or fragment thereof, such as the N-terminal extracellular domain fragment or the C-terminal cytoplasmic CAML-binding domain fragment, may be derivatized by the attachment of one or more chemical moieties to the protein moiety. Chemical modification of biologically active component or components may provide additional advantages under certain circumstances, such as increasing the stability and circulation time of the component or components and decreasing immunogenicity. See U.S. Pat. No. 4,179,337, Davis et al., issued Dec. 18, 1979. For a review, see Abuchowski et al., in *Enzymes as Drugs* [J. S. Holcerberg and J. Roberts, eds. pp. 367–383 (1981)]. A review article describing protein modification and fusion proteins is Francis, *Focus on Growth Factors*, 3:4–10 (1992), Mediscript: Mountview Court, Friern Barnet Lane, London N20, OLD, UK.

The chemical moieties suitable for derivatization may be selected from among water soluble and water insoluble polymers, with water soluble polymers preferred. The polymer selected should preferably be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations.

For the present component or components, these may be ascertained using the assays provided herein.

Labeled TACI proteins. The TACI protein of the present invention, and fragments thereof, may be labeled. Suitable labels include enzymes, fluorophores (e.g., fluorescence isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the test sample and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}$, $^{131}$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radio nucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419–439 (1980) and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{14}$C]-amino acids and [$^{3}$H]-amino acids (with the tritium substituted at non-labile positions).

Chimeric TACI Proteins

A chimeric TACI protein of the invention may be a protein that is generated by joining a functional domain of a TACI protein, such as the ligand binding domain or the CAML-binding domain, with the complementary domain of another protein, e.g., an alternative receptor. Chimeric constructs can also be prepared with a functionally active fragment of a TACI protein and another functionally active molecule. For example, the extracellular domain of a TACI protein may be joined to the Fc domain of an immunoglobulin. Alternatively, the cytoplasmic domain of a TACI protein could be joined to a receptor ligand, such as transferrin or a hormone, for intracellular targeting. In yet another embodiment, a TACI domain could be joined to another targeting molecule, such as an anti-immunoglobulin heavy chain or light chain molecule (e.g., an Fv portion of an antibody) to specifically target B cells. In still another embodiment, the functionally active fragment of a TACI protein, preferably the N-terminal extracellular domain, can be joined with a glycosylphospholipid, such as glycosylphosphoinositol, anchor signal sequence, preferably located at the C-terminus of the TACI fragment, so that a glycolipid anchored protein is generated [Cross, *Annu. Rev. Cell Biol.*, 6:1–39 (1990); Low, *Biochem. J.*, 244:1–13 (1987)].

A chimeric TACI receptor can be prepared by joining the extracellular domain of another receptor molecule with a transmembrane domain and the intracellular domain of a TACI protein. In another embodiment, the extracellular domain of TACI can be joined with a transmembrane domain and an intracellular domain of another receptor molecule. The transmembrane domain can be the transmembrane domain of a TACI protein, the transmembrane domain of the other receptor, or a different transmembrane domain. Preferably, the transmembrane domain is from the same protein component of the chimera as the extracellular domain. Chimeric receptors have been described [International Patent Publications WO96/23814; WO96/23881; and WO96/24671]. Chimeric antigen receptors have been described [Capon et al., U.S. Pat. No. 5,359,046, issued Oct. 25, 1994], including functional antigen-specific receptors generated in B cells [Sanchez et al., *J. Exp. Med.*, 178:1049–1055 (1993)] and T cells [Burkhardt et al., *Mol. Cell. Biol.*, 14:1095–1103 (1994)] by fusing the Igα and Igβ signal transduction chains to IgM. Various type I and type II cytokine receptors, including interferon-α, interferon-β, interferon-γ, interleukin-1, interleukin-2, interleukin-3, interleukin-4, interleukin-6, interleukin-8, interleukin-10, interleukin-12, erythropoietin, granulocyte-macrophage colony stimulating factor (CSF), granulocyte-CSF, macrophage-CSF, α-chemokine receptors, and β-chemokine receptors, can provide complementary components in a chimeric receptor comprising a functionally active fragment of a TACI protein.

As those of ordinary skill in the art can appreciate, transmembrane domains are generally functionally equivalent for anchoring a protein in a membrane. However, the presence of specific amino acid residues in a transmembrane domain can affect receptor interaction with, e.g., dimerization, or association with other integral membrane proteins, such as in a multi-protein receptor complex. Thus, selection of a transmembrane domain depends on whether regulatory functions performed by the transmembrane domain are desired or necessary.

Nucleic Acids Encoding TACI Proteins

The present invention contemplates isolation of a gene encoding a TACI protein including a full length, or naturally occurring form of TACI protein, and any antigenic fragments thereof from any animal, particularly mammalian and more particularly human, source. As used herein, the term "gene" refers to an assembly of nucleotides that encode a polypeptide, and includes cDNA and genomic DNA nucleic acids.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5×or 6×SCC. High stringency hybridization conditions correspond to the highest $T_m$, e.g., 50% formamide, 5×or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least 10 nucleotides; preferably at least 18 nucleotides; more preferably the length is at least 24 nucleotides and most preferably at least 30 nucleotides in length. In a specific embodiment, a hybridizable nucleic acid of the invention has a sequence corresponding to at least 12 nucleotides, preferably at least 18 nucleotides, more preferably at least 24 nucleotides, and most preferably at least 30 nucleotides in length of SEQ ID NO:1, or more specifically the coding sequence of SEQ ID NO:1.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

As used herein, the term "oligonucleotide" refers to a nucleic acid, generally of at least 18 nucleotides, that is hybridizable to a genomic DNA molecule, a cDNA molecule, or an mRNA molecule encoding a TACI protein. Oligonucleotides can be labeled, e.g., with $^{32}$P-nucleotides or nucleotides to which a label, such as biotin, has been covalently conjugated (see the discussion, supra, with respect to labeling TACI polypeptides). In one embodiment, a labeled oligonucleotide can be used as a probe to detect the presence of a nucleic acid encoding a TACI protein. In another embodiment, oligonucleotides (one or both of which may be labeled) can be used as PCR primers, either for cloning full length or a fragment of a TACI protein, or to detect the presence of nucleic acids encoding a TACI protein. In a further embodiment, an oligonucleotide of the invention can form a triple helix with a TACI DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence. In a specific embodiment, a TACI coding sequence of the invention has the nucleotide sequence depicted in SEQ ID NO:1.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" may be included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence.

Translocation signal sequences can be found associated with a variety of proteins native to eukaryotes and prokaryotes, and are often functional in both types of organisms. Interestingly, the TACT of the invention is transported so that the N-terminus is extracellular in the absence of a cleaved signal sequence. Thus, this transmembrane protein is a type III transmembrane protein [see Wilson-Rawls et al., *Virology* , 201:66–76 (1994)]. Thus, in a construct of the present invention (including a chimeric construct as discussed above), if the N-terminal portion of the construct encodes the N-terminus of TACI, a signal peptide may not be required to obtain expression of the transmembrane TACI protein.

As used herein, the term "sequence homology" in all its grammatical forms refers to the relationship between proteins that possess a "common evolutionary origin, " including proteins from superfamilies (e.g., the immunoglobulin superfamily) and homologous proteins from different species (e.g., myosin light chain, etc.) [Reeck et al., *Cell,* 50:667 (1987)]. The present invention naturally contemplates homologues of the human TACI protein as falling within the scope of the invention.

Accordingly, the term "sequence similarity" in all its grammatical forms refers to the degree of identity or correspondence between nucleic acid or amino acid sequences whether or not they share a common evolutionary origin (see Reeck et al., supra). In common usage, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. The present invention contemplates nucleotides that are 50% similar to SEQ ID NO:1 (or its complementary sequence), preferably 60% similar, and more preferably 75% similar. Preferably such substantially similar nucleic acids are homologous.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding a TACI protein, whether genomic DNA or cDNA, can be isolated from any source, particularly from a human cDNA or genomic library. Methods for obtaining TACI protein gene are well known in the art, as described above (see, e.g., Sambrook et al., 1989, supra).

Accordingly, any animal cell potentially can serve as the nucleic acid source for the molecular cloning of a TACI protein gene. The DNA may be obtained by standard procedures known in the art from cloned DNA (e.g., a DNA "library"), and preferably is obtained from a cDNA library prepared from tissues with high level expression of the protein (e.g., a thymic cDNA library, since peripheral blood cells and in particular lymphocyte cells, appear to have the highest levels of expression of TACI protein), by chemical synthesis, by CDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired TACI protein gene may be accomplished in a number of ways. For example, a portion of a TACI protein gene or its specific RNA, or a fragment thereof, can be purified and labeled, the generated DNA fragments may then be screened by nucleic acid hybridization to the labeled probe [Benton and Davis, *Science,* 196:180 (1977)]; [Grunstein and Hogness, *Proc. Natl. Acad. Sci. U.S.A.,* 72:3961 (1975)]. For example, a set of oligonucleotides corresponding to the partial amino acid sequence information obtained for the TACI protein can be prepared and used as probes for DNA encoding a TACI protein, or as primers for cDNA or MRNA (e.g., in combination with a poly-T primer for RT-PCR). Preferably, a fragment is selected that is highly unique to the TACI protein of the invention. Those DNA fragments with substantial homology to the probe will hybridize. As noted above, the greater the degree of homology, the more stringent hybridization conditions can be used. In a specific embodiment, stringency hybridization conditions are used to identify a homologous TACI protein gene.

Further selection can be carried out on the basis of the properties of the gene, e.g., if the gene encodes a protein product having the isoelectric, electrophoretic, amino acid composition, or partial amino acid sequence of the TACI protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for TACI protein.

A TACI protein gene of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified TACI protein DNA, or may be synthetic oligonucleotides designed from the partial amino acid sequence information. Immunoprecipitation analysis or functional assays (e.g., CAML binding activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against TACI protein, such as the rabbit polyclonal anti-human TACI protein antibody described herein.

A radiolabeled TACI protein cDNA can be synthesized using the selected mRNA (from the adsorbed polysomes) as a template. The radiolabeled mRNA or cDNA may then be used as a probe to identify homologous TACI protein DNA fragments from among other genomic DNA fragments.

The present invention also relates to cloning vectors containing genes encoding analogs and derivatives of the TACI protein of the invention, that have the same or homologous functional activity as TACI protein, and homologs thereof from other species. The production and use of derivatives and analogs related to TACI protein are within the scope of the present invention. In a specific embodiment, the derivative or analog is functionally active, i.e., capable of exhibiting one or more functional activities associated with a full-length, wild-type TACI protein of the invention. In another embodiment, TACI protein containing a different cytoplasmic domain, e.g., one unable to bind CAML but still able to modulate the activation of AP-1. In another aspect, a TACI protein of the invention can be prepared with a lectin domain or domains from another protein, such as the mannose receptor of macrophages or the phospholipase receptor on muscle.

TACI protein derivatives can be made by altering encoding nucleic acid sequences by substitutions, additions or deletions that provide for functionally equivalent molecules. Preferably, derivatives are made that have enhanced or increased functional activity relative to native TACI protein. Alternatively, such derivatives may encode soluble fragments of TACI protein extracellular domain that have the same or greater affinity for the natural ligand of TACI protein of the invention. Such soluble derivatives may be potent inhibitors of ligand binding to TACI protein.

Due to the degeneracy of nucleotide coding sequences, other DNA sequences which encode substantially the same amino acid sequence as a TACI protein gene may be used in the practice of the present invention. These include but are not limited to allelic genes, homologous genes from other species, and nucleotide sequences comprising all or portions of TACI protein genes which are altered by the substitution of different codons that encode the same amino acid residue within the sequence, thus producing a silent change. Likewise, the TACI protein derivatives of the invention include, but are not limited to, those containing, as a primary amino acid sequence, all or part of the amino acid sequence of a TACI protein including altered sequences in which functionally equivalent amino acid residues are substituted for residues within the sequence resulting in a conservative amino acid substitution. And thus, such a substitution is defined as a conservative substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding TACI protein derivatives and analogs of the invention can be produced by various methods known in the art. The manipulations which result in their production can occur at the gene or protein level. For example, the cloned TACI protein gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of TACI protein, care should be taken to ensure that the modified gene remains within the same translational reading frame as the TACI protein gene, uninterrupted by translational stop signals, in the gene region where the desired activity is encoded.

Additionally, the TACI protein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated TACI protein gene product. Any technique for mutagenesis known in the art can be used, including but not limited to, in vitro site-directed mutagenesis [Hutchinson, C., et al., *J. Biol. Chem.,* 253:6551 (1978)]; [Zoller and Smith, *DNA,* 3:479–488 (1984)]; [Oliphant et al., *Gene,* 44:177 (1986)]; [Hutchinson et al., *Proc. Natl. Acad. Sci. U.S.A.,* 83:710 (1986)], use of TABS® linkers (Pharmacia), etc. PCR techniques are preferred for site directed mutagenesis (see Higuchi, "Using PCR to Engineer DNA", in PCR *Technology: Principles and Applications for DNA Amplification,* H. Erlich, ed., Stockton Press, Chapter 6, pp. 61–70 (1989)).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Transmembrane Activator and CAML Interactor Polypeptides

The nucleotide sequence coding for the TACI protein, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding the TACI protein of the present invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding a TACI protein and/or its flanking regions.

As pointed out above, potential chimeric partners for TACI protein include those having lectin domains, either from naturally occurring multivalent lectin receptors, such as mannose receptor of macrophages, natural lectins, or other sources, or a substitute cytoplasmic domain, capable of mediating signal transduction or modifying the endocytic processing.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant TACI protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell containing the recombinant vector comprising the nucleic acid encoding a TACI protein is cultured in an appropriate cell culture medium under conditions that provide for expression of TACI protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of TACI protein may be controlled by any promoter/enhancer element known in the art, but these regulatory elements must be functional in the host selected for expression. Promoters which may be used to control TACI protein gene expression include, but are not limited to, the SV40 early promoter region [Benoist and Chambon, *Nature*, 290:304–310 (1981)], the promoter contained in the 3' long terminal repeat of Rous sarcoma virus [Yamamoto, et al., *Cell*, 22:787–797 (1980)], the herpes thymidine kinase promoter [Wagner t al., *Proc. Natl. Acad. Sci. U.S.A.*, 78:1441–1445 (1981)], the regulatory sequences of the metallothionein gene [Brinster et al., *Nature*, 296:39–42 (1982)]; prokaryotic expression vectors such as the βlactamase promoter [Villa-Kamaroff, et al., *Proc. Natl. Acad. Sci. U.S.A.*, 75:3727–3731 (1978)], or the tac promoter [DeBoer, et al., *Proc. Natl. Acad. Sci. U.S.A.*, 80:21–25 (1983)]; see also "Useful proteins from recombinant bacteria" in Scientific American, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell*, 38:639–646 (1984)]; [Ornitz et al., *Cold Spring Harbor Symp. Quant. Biol.*, 50:399–409 (1986)]; [MacDonald, *Hepatology*, 7:425–515 (1987)]; insulin gene control region which is active in pancreatic beta cells [Hanahan, *Nature*, 315:115–122 (1985)], immunoglobulin gene control region which is active in lymphoid cells [Grosschedl et al., *Cell*, 38:647–658 (1984)]; [Adames et al., *Nature*, 318:533–538 (1985)]; [Alexander et al., *Mol. Cell. Biol.*, 7:1436–1444 (1987)], mouse mammary tumor virus control region which is active in testicular, breast, lymphoid and mast cells [Leder et al., *Cell*, 45:485–495 (1986)], albumin gene control region which is active in liver [Pinkert et al., *Genes and Devel.*, 1:268–276 (1987)], alpha-fetoprotein gene control region which is active in liver [Krumlauf et al., *Mol. Cell. Biol.*, 5:1639–1648 (1985)]; [Hammer et al., *Science*, 235:53–58 (1987)], alpha 1-antitrypsin gene control region which is active in the liver [Kelsey et al., *Genes and Devel.*, 1:161–171 (1987)], beta-globin gene control region which is active in myeloid cells [Mogram et al., *Nature*, 315:338–340 (1985)]; [Kollias et al., Cell, 46:89–94 (1986)], myelin basic protein gene control region which is active in oligodendrocyte cells in the brain [Readhead et al., Cell, 48:703–712 (1987)], myosin light chain-2 gene control region which is active in skeletal muscle [Sani, Nature, 314:283–286 (1985)], and gonadotropic releasing hormone gene control region which is active in the hypothalamus [Mason et al., Science, 234:1372–1378 (1986)].

Expression vectors containing a nucleic acid encoding a TACI protein of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a TACI protein is inserted within the "selection marker" gene sequence of the vector, recombinants containing the TACI protein insert can be identified by the absence of the TACI protein gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMal-C2, pET, pGEX [Smith et al., Gene, 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Sunmmers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible metallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammnalian expression vectors (see, Kaufman, 1991, supra) for use according to the invention include but are not limited to pSC11 (SmaI cloning site, TO- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the TACI protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage e.g., of signal sequence) of proteins. Appropriate cell lines or host systems can be chosen to ensure the desired modification and processing of the foreign protein expressed. For example, expression in a bacterial system can be used to produce an non-glycosylated core protein product.

Vectors are introduced into the desired host cells by methods known in the art, e.g., transfection, electroporation, micro injection, transduction, cell fusion, DEAE dextran, calcium phosphate precipitation, lipofection (lysosome fusion), use of a gene gun, or a DNA vector transporter (see, e.g., Wu et al., *J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990).

Gene Therapy and Transgenic Vectors

A genetic deficiency of a TACI protein can be one of the many factors involved in inherited immunodeficiency. The present invention includes gene therapy with the TACIprotein cDNA that restores normal lymphocyte function in patients having a genetic defect in the Transmembrane Activator and CAML Interactor protein gene. The present invention also includes modified forms of TACI to be used as gene-therapeutic tools through inserting them into blood stem cells in preparation for re-infusion into patients as part of bone marrow transplant regimes. In one embodiment an epitope tagged-TACI derivative is used as a way to selectively activate only those lymphocytes derived from the marrow transplant by injection of the specific antibody into the patient. In an alternative embodiment transduction of a TACI gene lacking its intracellular portion is used to create a relatively innocuous lymphocyte with diminished responsiveness. This embodiment is useful in autoimmune diseases involving activation of B cells.

In one embodiment, a gene encoding a TACI protein or polypeptide domain fragment thereof is introduced in vivo in a viral vector. Such vectors include an attenuated or defective DNA virus, such as but not limited to herpes simplex virus (HSV), papilloma virus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, lymphocytes can be specifically targeted. Examples of particular vectors include, but are not limited to, a defective herpes virus 1 (HSV1) vector [Kaplitt et al., *Molec. Cell. Neurosci.*, 2:320–330 (1991)], an attenuated adenovirus vector, such as the vector described by Stratford-PerricaudetI [*J. Clin. Invest.*, 90:626–630 (1992)], and a defective adeno-associated virus vector [Samulski et al., *J. Virol,.* 61:3096–3101 (1987)]; [Samulski et al., *J. Virol.*, 63:3822–3828 (1989)].

Preferably, for in vivo administration, an appropriate immunosuppressive treatment is employed in conjunction with the viral vector, e.g., adenovirus vector, to avoid immunodeactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., *J. Virol.*, 62:1120 (1988); Temin et al., U.S. Pat. No. 5,124,263; International Patent Publication No. WO 95/07358, published Mar. 16, 1995, by Dougherty et al.; and Kuo et al., Blood, 82:845 (1993).

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.*, 84:7413–7417 (1987); see Mackey, et al., *Proc. Natl. Acad. Sci. U.S.A.*, 85:8027–8031 (1988)]. The use of cationic lipids may promote encapsulation of negatively charged nucleic acids, and also promote fusion with negatively charged cell membranes [Felgner and Ringold, *Science*, 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, micro injection, transduction, cell fusion, DEAE dextran, calcium phosphate precipitation, use of a gene gun, or use of a DNA vector transporter [see, e.g., Wu et al., *J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990].

In a preferred embodiment of the present invention, a gene therapy vector as described above employs a transcription control sequence operably associated with the sequence for the TACI protein inserted in the vector. That is, a specific expression vector of the present invention can be used in gene therapy.

Gene Targeting

As used herein "Gene targeting" is a type of homologous recombination that occurs when a fragment of genomic DNA is introduced into a mammalian cell and that fragment locates and recombines with endogenous homologous sequences.

As used herein a "knockout mouse" is a mouse that contains within its genome a specific gene that has been inactivated by the method of gene targeting. A knockout mouse includes both the heterozygote mouse (i.e., one defective allele and one wild-type allele) and the homozygous mutant (i.e., two defective alleles).

As used herein a "marker gene" is a selection marker that facilitates the isolation of rare transfected cells from the majority of treated cells in the population. A non-comprehensive list of such markers includes neomycin phosphotransferase, hygromycin B phosphotransferase, Xanthine/guanine phosphoribosyl transferase, herpes simplex thymidine kinase, and diphtheria toxin.

The functional activity of Transmembrane Activator and CAML Interactor protein can be evaluated transgenically. In this respect, a transgenic mouse model can be used. The TransmembraneActivator and CAML Interactorprotein gene can be used in complementation studies employing a transgenic mouse. Transgenic vectors, including viral vectors, or cosmid clones (or phage clones) corresponding to the wild type locus of a candidate gene, can be constructed using the isolated TACI protein gene. Cosmids may be introduced into transgenic mice using published procedures [Jaenisch, Science, 240:1468–1474 (1988)]. In a genetic sense, the transgene acts as a suppressor mutation.

Alternatively, a transgenic animal model can be prepared in which expression of the TACI protein gene is disrupted. Gene expression is disrupted, according to the invention, when no functional protein is expressed. One standard method to evaluate the phenotypic effect of a gene product is to employ knock-out technology to delete the gene. Alternatively, recombinant techniques can be used to introduce mutations, such as nonsense and amber mutations, or mutations that lead to expression of an inactive protein. In another embodiment, TACI protein genes can be tested by examining their phenotypic effects when expressed in antisense orientation in wild-type animals. In this approach, expression of the wild-type allele is suppressed, which leads to a mutant phenotype. RNA-RNA duplex formation (antisense-sense) prevents normal handling of mRNA, resulting in partial or complete elimination of wild-type gene effect. This technique has been used to inhibit TK synthesis in tissue culture and to produce phenotypes of the Kruppel mutation in Drosophila, and the Shiverer mutation in mice [Izant et al., Cell, 36:1007–1015 (1984); Green et al., Annu. Rev. Biochem., 55:569–597 (1986); Katsuki et al., Science, 241:593–595 (1988)]. An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 polyA site. This transgene will be used to make transgenic mice, or by using gene knockout technology.

Thus the present invention extends to the preparation of antisense nucleotides and ribozymes that may be used to interfere with the expression of the TACI protein at the translational level. This approach utilizes antisense nucleic acid and ribozymes to block translation of a specific mRNA, either by masking that mRNA with an antisense nucleic acid or cleaving it with a ribozyme. Genes encoding TACI mRNA-specific antisense or ribozyme nucleic acids can be introduced, e.g., using techniques as described above for "Gene Therapy." Alternatively, synthetic antisense or ribozyme oligonucleotides can be prepared.

Antisense nucleic acids are DNA or RNA molecules that are complementary to at least a portion of a specific mRNA molecule [see Marcus-Sekura, Anal. Biochem., 172:298 (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al., J. Exp. Med., 168:1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Investigators have identified two types of ribozymes, Tetrahymena-type and "hammerhead"-type. Hammerhead-type ribozymes are preferable to Tetrahymena-type ribozymes for inactivating a specific mRNA species, and eighteen base recognition sequences are preferable to shorter recognition sequences.

The DNA sequences encoding the TACI protein described and enabled herein may thus be used to prepare antisense molecules against and ribozymes that cleave mRNAs for the TACI protein, thus inhibiting expression of the gene encoding the TACI protein, which may reduce the level of immune stimulation by dendritic cells, or the level of clonal detection by mediated by thymic epithelial cells.

Gene targeting in embryonic stem cells is a relatively new technique that allows the precise manipulation of genes in vivo. This technique allows the creation of mice with defined mutations in the structure of any given gene. This ability to generate predetermined mutations gives investigators the ability to apply the power of genetics to the complex human immune system, as it has successfully been applied in neuronal systems for such organisms as Drosophila and C. elegans.

A key to finding treatments for many disorders has been the development of appropriate animal models. The present invention includes a knockout mouse containing a non-functional allele for the gene that naturally encodes and expresses functional TACI protein. Included within this aspect of the invention is a knockout mouse containing two non-functional alleles for the gene that naturally encodes and expresses functional TACI protein, and therefore is unable to express functional TACI protein.

Non-functional alleles can be generated in any number of ways that are well known in the art, all of which may be used in the present invention. In some embodiments, a non-functional allele is made defective by an insertion of extraneous DNA into the coding region of TACI protein allele. In a preferred embodiment, the insertion is placed in the first exon of the coding region of the TACI protein gene. In more preferred embodiments, the insertion contains a signal to terminate transcription prior to the transcription of a region of the allele that encodes TACI protein. In these preferred embodiments it is still more preferred to remove a section of DNA at the beginning of the coding region for the TACI protein and replacing it with the above insertion.

The present invention also includes a method for producing the knockout mouse of the instant invention that includes: obtaining genomic DNA encoding a TACI protein, constructing a vector containing said genomic DNA and a marker gene wherein said marker gene is placed within the exon of said genomic DNA. The vector is then electroporated into an embryonic stem cell and an embryonic stem cell is selected that has integrated the vector into the genome, wherein the selected cell has integrated the marker gene into the endogenous site of the gene for the TACI protein in the mouse genome. The cell is then injected into a mouse blastocyst which is then re-implanted into a pseudopregnant female mouse, which gives birth to a chimeric mouse containing a defective allele for the TACI protein in its germ line. The chimeric mouse is then mated to a mouse of a standard in-bred line to generate a heterozygous knockout mouse. Two heterozygous mice are then bred generating a homozygous knockout mouse offspring. Detailed protocols for successful gene targeting are well known in the art, and for example as described by Joyner, A. L. (1993) *Gene Targeting: A Practical Approach*. The Practical Approach Series (Rickwood, D., and Hames, B. D., Eds.), IRL Press, Oxford which is hereby incorporated by reference in its entirety.

Another aspect of the invention is a method for selecting a therapeutic agent for possible use as an immunosuppressant which comprises administering a suspected therapeutic agent to the knockout mouse of the present invention and measuring and/or determining the putative therapeutic agent's effect on any of the phenotypic characteristics which may be believed to be related to the immunodeficiency.

A preferred embodiment of this aspect of the invention includes administering a suspected therapeutic agent to the knockout mouse of the present invention and measuring a test response in the knockout mouse, wherein the normal response of the knockout mouse in the absence of a therapeutic agent is characteristically different from that of wild-type mice. The potential therapeutic agents are selected on the basis of whether there is a statistical significance between test response and the normal response. Potential therapeutic agents are selected that show a statistically significant change in the characteristic measured/determined.

In a preferred embodiment, the normal response of the knockout mouse in the absence of a therapeutic agent is characteristically different by being characteristically lower than that of wild-type mice and the selected therapeutic agents act to raise the sensitivity of that characteristic.

The suspected therapeutical agents may be obtained from any number of drug or peptide libraries including those commercially available from drug chemical companies.

Purification of TACI Proteins and Homologues Thereof

The TACI protein of the present invention and homologues thereof can be purified by any number of procedures that encompass a wide variety of known purification steps. Those with skill in the art would know to refer to references, such as the Methods of Enzymology series, for greater detail and breadth. Initial steps for purifying the proteins of the present invention include salting in or salting out, such as in ammonium sulfate fractionations; solvent exclusion fractionations, e.g., an ethanol precipitation; detergent extractions to free membrane bound proteins using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxy propyl] amino ethyl (QAE) Sephadex or cellulose; or with a cation exchanger such as carboxymethyl (CM) or sulfo propyl (SP) Sephadex or cellulose. Alternative means of solid phase binding includes the exploitation of hydrophobic interactions e.g., the using of a solid support such as phenylSepharose and a high salt buffer; affinity-binding, using, e.g., CAML (or a TACI-binding fragment thereof) bound to an activated support; immuno-binding, using e.g., an antibody to the TACI protein bound to an activated support; as well as other solid phase supports including those that contain specific dyes or lectins etc. A further solid phase support technique that is often used at the end of the purification procedure relies on size exclusion, such as Sephadex and Sepharose gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a biological buffer at a pH close to the pKa of that buffer. Typical buffers can be purchased from most biochemical catalogues and include the classical buffers such as Tris, pyrophosphate, monophosphate, and diphosphate, or the Good buffers [Good, N. E., et al., *Biochemistry*, 5:467 (1966)]; [Good, N. E. and Izawa, S., *Meth. Enzymol.*, 24, Part B, 53 (1972)]; and [Fergunson, W. J. and Good, N. E., *Anal. Biochem.*, 104:300 (1980)] such as Mes, Hepes, Mops, tricine and Ches.

Materials to perform all of these techniques are available from a variety of sources such as Sigma Chemical Company in St. Louis, Mo.

Antibodies to the TACI Protein

The present invention discloses the protein sequence and properties of a specific Transmembrane Activator and CAML Interactor protein, TACI, thereby enabling the development of antibody reagents specific for the extracellular portion of the receptor. Polyvalent antibody reagents can act to cross-link and activate TACI signaling in lymphocytes, a useful process in situations where enhanced lymphocyte responsiveness is beneficial. Such situations include for example, in the treatment of immunodeficiencies that are either congenital or acquired e.g., AIDS. In addition, these antibody reagents may be used as an adjuvant treatment in cancer in instances that the immune system can aid in the eradication of neoplastic cells. Similarly monovalent antibody reagents can act to block access to TACI in lymphocytes, a process that is useful in situations where depressed lymphocyte responsiveness is beneficial such as during organ transplants.

According to the present invention, the TACI protein produced naturally, recombinantly or by chemical synthesis, and fragments or other derivatives or analogs thereof, including fusion proteins, may be used as an immunogen to generate antibodies that recognize the TACI protein. Such antibodies include but are not limited to polyclonal, monoclonal, chimeric, single chain, Fab fragments, and an Fab expression library. The anti-TACI protein antibodies of the invention may be cross reactive, e.g., they may recognize the TACI protein from different species. Polyclonal antibodies have greater likelihood of cross reactivity. Alternatively, an antibody of the invention may be specific for a single form of the TACI protein. Preferably, such an antibody is specific for human TACI protein. Antibodies of the invention can be labeled, as described above for TACI proteins and polypeptides.

Various procedures known in the art may be used for the production of polyclonal antibodies to the TACI protein or derivative or analog thereof. For the production of antibody, various host animals can be immunized by injection with the TACI protein, or a derivative (e.g., fragment or fusion protein) thereof, including but not limited to rabbits, mice, rats, sheep, goats, etc. In one embodiment, the TACI protein or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monoclonal antibodies directed toward the TACI protein, or fragment, analog, or derivative thereof, any technique that provides for the production of antibody molecules by continuous cell lines in culture may be used. These include but are not limited to the hybridoma technique originally developed by Kohler and Milstein [Nature, 256:495–497 (1975)], as well as the trioma technique, the human B-cell hybridoma technique [Kozbor et al., *Immunology Today,* 4:72 (1983)]; [Cote et al., *Proc. Natl. Acad. Sci. U.S.A.,* 80:2026–2030 (1983)], and the EBV-hybridoma technique to produce human monoclonal antibodies [Cole et al., in *Monoclonal Antibodies and Cancer Therapy,* Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.,* 159:870 (1984); Neuberger et al., *Nature,* 312:604–608 (1984); Takeda et al., *Nature,* 314:452–454 (1985)] by splicing the genes from a mouse antibody molecule specific for a TACI protein together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogeneic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce the TACI protein-specific single chain antibodies. An additional embodiment of the invention utilizes the techniques described for the construction of Fab expression libraries [Huse et al., *Science,* 246:1275–1281 (1989)] to allow rapid and easy identification of monoclonal Fab fragments with the desired specificity for a TACI protein, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a TACI protein, one may assay generated hybridomas for a product which binds to a TACI protein fragment containing such epitope. For selection of an antibody specific to a TACI protein from a particular species of animal, one can select on the basis of positive binding with the TACI protein expressed by or isolated from cells of that species of animal.

The foregoing antibodies can be used in methods known in the art relating to the localization and activity of the TACI protein, e.g., for Western blotting, imaging the TACI protein in situ, measuring levels thereof in appropriate physiological samples, etc. using any of the detection techniques mentioned above or known in the art.

In a specific embodiment, antibodies that agonize or antagonize the activity of the TACI protein can be generated. Such antibodies can be tested using the assays described infra for identifying ligands.

Ligands to the TACI Protein

The identity of the endogenous ligand of the TACI protein is unknown. The TACI protein can be used, to screen clones in order to identify the endogenous ligand(s). This ligand is likely to be involved in the regulation of the immune system as well, and thus should have similar or complementary uses to those described herein. Methods for screening for TACI-1 ligands include: (i) through the use of a yeast two-hybrid system with TACI-1 as "bait", as described, e.g., in Chien et al., *Proc. Natl. Science, USA,* 88:9578–9582 (1991) and Durfee et al., *Genes Dev.,* 7:555–69 (1993); (ii) interaction cloning from *E. coli* expression-libraries as described above; and (iii) functional expression cloning in mammalian cells as described above.

Identification and isolation of a gene encoding a TACI protein of the invention provides for expression of the TACI protein or fragments thereof in quantities greater than can be isolated from natural sources, or in cells that are specially engineered to be regulated by the TACI protein expressed after transfection or transformation of the cells. Accordingly, in addition to rational design of agonists and antagonists based on the structure of the TACI protein, the present invention contemplates an alternative method for identifying specific ligands of the TACI protein using various screening assays known in the art.

Any screening technique known in the art can be used to screen for TACI protein agonists or antagonists. The present invention contemplates screens for small molecule ligands or ligand analogs and mimics, as well as screens for the natural ligand(s) that bind to and agonize or antagonize the TACI protein in vivo. For example, natural products libraries can be screened using assays of the invention for molecules that agonize or antagonize the TACI protein activity, or that bind to the extracellular domain or cytoplasmic domain of TACI.

Knowledge of the primary sequence of the TACI protein, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, *Science*, 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology*, 23:709–715 (1986); Geysen et al., *J. Immunologic Method*, 102:259–274 (1987)] and the method of Fodor et al. [*Science*, 251:767–773 (1991)] are examples. Furka et al. [*14th International Congress of Biochemistry*, Volume 5, Abstract FR:013 (1988); Furka, *Int. J. Peptide Protein Res.*, 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA*, 90:10700–4 (1993); Ohlmeyer et al., *Proc. Natl. Acad. Sci. USA*, 90:10922–10926 (1993); Lam et al., International Patent Publication No. WO 92/00252; Kocis et al., International Patent Publication No. WO 9428028, each of which is incorporated herein by reference in its entirety], and the like can be used to screen for the TACI protein ligands according to the present invention.

Alternatively, assays for binding of soluble ligand to cells that express recombinant forms of the TACI N-Terminal extracellular domain can be performed. The soluble ligands can be provided readily as recombinant or synthetic polypeptides.

The screening can be performed with recombinant cells that express TACI, or a fragment thereof, or alternatively, using purified protein, e.g., produced recombinantly, as described above. For example, the ability of labeled, soluble or solubilized TACI fragment to bind ligand can be used to screen libraries, as described in the foregoing references.

Screening For Novel Immunosuppressant Drugs

Certain diseases result from over activation of the B-lymphocyte response. One example is Systemic Lupus Erythematosus (SLE), in which antibodies are created that react with antigens (proteins, DNA, etc.) naturally present in the patient. The antibodies form complexes with the antigens, and circulate as reactive protein agglomerates. These complexes deposit in different organs and lead to the many symptoms of SLE, including kidney failure, neurologic symptoms, and death. Current treatments include the use of relatively non-specific immunosuppressants such as cyclosporin A or steroids which suppress responses in both T and B cells. Although they can often effectively treat SLE and similar diseases, there is a significant risk of over-immunosuppression, in which the patient develops serious infections because of lack of functioning T-cells. A new immunosuppressant drug that selectively blocks the action of B-lymphocytes, while leaving T-cells intact to protect patients from viral pathogens would be extremely useful to treat these diseases. Therefore, TACI-1 can be used as a novel tool for developing immunosuppressant drugs specific for B-lymphocytes.

The TACI protein is not naturally present in mature T-lymphocytes or Jurkat T cells, a cell line that has phenotypic characteristics of mature T-cells. Indeed, the highest level of expression of the TACI protein is on peripheral B lymphocytes, whereas peripheral T-cells do not express the TACI protein. However, Jurkat T cells can be transfected with a TACI expression plasmid and the TACI expressed can be readily stimulated by cross linking to a TACI specific antibody. This stimulation leads to the activation of a pair of second messenger pathways that are both necessary and sufficient to stimulate the early T-cell transcription factor NF-AT.

In a particular embodiment Jurkat T cells are transfected with TACI-1 expression plasmid and a NF-AT-reporter plasmid. Jurkat T cells naturally express the T-cell receptor (TCR). The cells are stimulated by the addition of antibodies to TACI-1, antibodies to TCR, or antibodies to both. Candidate drugs are mixed with the Jurkat T cells and the effect of these drugs is determined. Phage and chemical libraries described above may be used as sources for drug candidates.

These candidate drugs are then applied in a parallel experiment in which antibodies to TCR are used in place of the antibodies to TACI-1. If the candidate drug has no effect on the SEAP signal stimulation due to the antibody-dependent activation of TCR, the candidate drug is identified as having selective inhibition of the TACI-1 activated response. Such selected drugs include that class of drugs which can selectively inhibit the B-cell (antibody producing) response, while allowing T-cell mediated (cellular) immunity to proceed. Such selected drugs may be used to treat the autoimmune diseases described above. Because TACI-1 activates lymphocytes by a novel mechanism (i.e. through direct contact with CAML) it is likely that a significant number of drugs are discoverable that can interfere with the CAML-dependent pathway, yet leave normal signaling through the T-cell receptor intact.

In a preferred embodiment of this type, the NF-AT-reporter plasmid contains the SEAP reporter. This signal is used to measure the degree of inhibition of activation. The SEAP reporter assay can be scaled up so as to be performed by a robot screening apparatus. Drugs that block the activation of TACI-1 but not TCR as measured by the SEAP reporter assay are identified as having selective inhibition of the TACI-1 activated response.

Alternatively, a phage library can be employed. Phage libraries have been constructed which when infected into host *E. coli* produce random peptide sequences of approximately 10 to 15 amino acids [Parmley and Smith, *Gene,* 73:305–318 (1988), Scott and Smith, *Science,* 249:386–249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of a TACI protein containing the N-terminal extracellular domain e.g., for human TACI-1 it is a peptide having the amino acid sequence of SEQ ID NO:6. After a specified incubation period, the filters can be thoroughly washed and developed for autoradiography. Plaques containing the phage that bind to the radioactive N-terminal extracellular domain can then be identified. These phages can be further cloned and then retested for their ability to inhibit the stimulation of TACI by an anti-TACI antibody while not inhibiting the corresponding stimulation of TCR as described above.

Once the phages have been purified, the binding sequence contained within the phage can be determined by standard DNA sequencing techniques. Once the DNA sequence is known, synthetic peptides can be generated which represents these sequences.

The effective peptide(s) can be synthesized in large quantities for use in in vivo models and eventually in humans as immunosuppressant drugs, for example. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, *Vaccine,* 10:175–178 (1990)].

Therapeutic Methods and Compositions

The Transmembrane Activator CAML Interactor protein of the present invention can activate two signals normally used to initiate cell growth and division. This receptor is likely to be involved in the neoplastic transformation of T or B lymphocytes in lymphoma or leukemia. Therefore, dominant negative forms of TACI-1 are useful to suppress growth of such cancer cells. Alternatively, TACI-1 over-stimulation can lead to programmed cell death. Taking advantage of this property, leukemia or lymphomas with TACI-1 cell surface expression may be induced to die by such over-stimulation. Activation of the TACI protein with antibody or crosslinking may activate an endogenous pathway leading to apoptosis. Binding with a monomeric form of an antibody or analogous ligand can block the TACI protein-associated endogenous pathway and interfere with growth simulation.

Therapeutic stimulation of TACI activity. As discussed above, the present invention advantageously provides for selective stimulation of the immune system by agonizing TACI activity. TACI agonists include the TACI ligand or ligands discovered as described supra, and antibodies that crosslink the receptor. Ligand agonists or antibody agonists can be administered as described below for treatment of subjects in whom immune stimulation, particularly of B cells, is desired.

B cell responses can be particularly important in fighting infectious diseases, including, but not limited to, bacterial, viral, protozoan, and parasitic infections. Antibodies against infectious microorganisms can rapidly immobilize the organisms by binding to antigen, followed by complement attack or cell mediated attack. Thus, a TACI agonist of the invention can be provided to a subject who is suffering from an infection to boost humoral immune responses. TACI agonists may be particularly useful for boosting immune responses after vaccination, during challenge with the infectious organism. Thus, subjects particularly at risk for infectious diseases, such as influenza, can supplement a vaccination or memory immunity with a TACI agonist during the flu season. Comparable immune boosting could be used with subjects who are entering or reentering an area with an endemic infectious disease, such as malaria.

In addition, B cell responses may be important in amplifying immune responses to tumors that express tumor-specific antigens. Thus, a TACI agonist may be provided where endogenous anti-tumor antibodies are detected. Indeed, B cells or plasma cells expressing anti-tumor cell surface immunoglobulin can be selected, such as by panning, and transduced with TACI to allow for an amplification of their antibody production.

In addition to amplifying beneficial immune responses, the present TACI agonists, e,g., ligands and antibodies, can be used to over-stimulate cells, such as B cells tumors (multiple myelomas, lymphomas, and leukemias), immature T cell tumors (leukemias and thymomas), and autoimmune or inflammatory cells and induce apoptosis in such cells, thereby reducing or eliminating the cancer or autoimmune/inflammatory condition.

Therapies for boosting cellular immune responses. Although TACI is found in only a subset of immature T cells, mature T cells can be transfected or transduced in vivo or ex vivo to express a functional TACI receptor, to amplify cellular immune responses. Preferably, tumor infiltrating cells are selected for such boosting, and reintroduced into the subject to more vigorously fight the tumor.

Therapeutic methods by antagonizing TACI activity. As discussed above, the present invention contemplates inhibiting TACI activity by various means, including but not limited to use of the free N-terminal extracellular domain; expression of a non-functional extracellular domain lacking a signal transduction domain, e.g., GPI-linked N-terminal TACI; use of antisense or ribozyme technologies to suppress expression of TACI; and use of TACI antagonist ligands or antibodies.

Suppression of TACI activity is useful for treating undesirable immune responses, including autoimmune and inflammatory diseases, transplantation rejection, and graft-versus host (GVH) disease. Autoimmune and inflammatory diseases include immune complex-induced vasculitis [Cochrane, *Springer Seminar Immunopathol.,* 7:263 (1984)], glomerulonephritis [Couser et al., *Kidney Inst.,* 29:879 (1985)], hemolytic anemia [Schreiber and Frank, *J. Clin. Invest.,* 51:575 (1972)], myasthenia gravis [Lennon, et al., *J. Exp. Med.,* 147:973 (1978); Biesecker and Gomez, *J. Immunol.,* 142:2654 (1989)], type II collagen-induced arthritis [Watson and Townes, *J. Exp. Med.,* 162:1878 (1985)], experimental allergic and hyperacute xenograft rejection [Knechtle, et al., *J. Heart Transplant,* 4(5):541

(1985); Guttman, Transplantation, 17:383 (1974); Adachi, et al., Trans. Proc., 19(1):1145 (1987)]; rheumatoid arthritis, and systemic lupus erythematosus (SLE).

In another embodiment, where a lymphocyte cancer such as myeloma, lymphoma, or leukemia expresses TACI, and TACI contributes to cancer growth, use of a TACI antagonist of the invention can be used to suppress the cancer cell growth.

Accordingly, a component of a therapeutic composition such as a polyvalent or mono-valent antibody of the present invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In another embodiment, the therapeutic compound can be delivered in a vesicle, in particular a liposome [see Langer, Science, 249:1527–1533 (1990); Treat et al., in Liposomes in the Therapy of Infectious Disease and Cancer, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing TACI.

In yet another embodiment, the therapeutic compound can be delivered in a controlled release system. For example, an agonist or antagonist to the transmembrane binding protein of the present invention, such as an antibody, may be administered using intravenous infusion, an implantable osmotic pump, a transdermal patch, liposomes, or other modes of administration. In one embodiment, a pump may be used [see Langer, supra; Sefton, CRC Crit. Ref. Biomed. Eng., 14:201 (1987); Buchwald et al., Surgery, 88:507 (1980); Saudek et al., N. Engl. J. Med., 321:574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem., 23:61 (1983); see also Levy et al., Science, 228:190 (1985); During et al., Ann. Neurol., 25:351 (1989); Howard et al., J. Neurosurg., 71:105 (1989)]. In yet another embodiment, a controlled release system can be placed in proximity of the therapeutic target, i.e., the brain, thus requiring only a fraction of the systemic dose [see, e.g., Goodson, in Medical Applications of Controlled Release, supra, vol. 2, pp. 115–138 (1984)]. Preferably, a controlled release device is introduced into a subject in proximity of the site of inappropriate immune activation or a tumor.

Other controlled release systems are discussed in the review by Langer (Science, 249:1527–1533 (1990).

In a further aspect, recombinant cells that have been transformed with the TACI protein gene and that express high levels of the polypeptide can be transplanted in a subject in need of the TACI protein. Preferably autologous cells transformed with TACI protein are transplanted to avoid rejection.

The therapeutic compounds of the present invention can be delivered by intravenous, intraarterial, intraperitoneal, intramuscular, or subcutaneous routes of administration. Alternatively, these compounds, properly formulated, can be administered by nasal or oral administration. A constant supply of these therapeutic compounds can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art A subject in whom administration of these therapeutic agents is an effective therapeutic regiment for an immunodeficiency disease is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The following examples are presented in order to more fully illustrate the preferred embodiments of the invention. They should in no way be construed, however, as limiting the broad scope of the invention.

EXAMPLE

Calcium Signaling by a Lymphocyte Surface Receptor Mediated through CAML

Introduction $Ca^{2+}$ influx is a key regulator of antigen-stimulated lymphocyte activation [Imboden et al., Immunol., 134:663–665 (1985)]; [Crabtree & Clipstone, Annu. Rev. Biochem., 63:1045–1083 (1994)]; [Weiss & Littman, Cell, 76:263–274 (1994)]. The CAML protein has been identified as a regulator of $Ca^{2+}$ signaling that is necessary but not sufficient for the activation of lymphocyte transcription factor, NF-AT (Bram & Crabtree, 1994, supra). The location of CAML in cytoplasmic vesicles is consistent with it regulating $Ca^{2+}$ influx by modulating intracellular $Ca^{2+}$ release. Here a novel human CAML-interacting receptor expressed by B lymphocytes that acts as a cell-surface signaling molecule is disclosed. This receptor, TACI (Transmembrane Activator CAML Interactor), initiates $Ca^{2+}$-dependent activation of NF-AT when cross linked with an antibody. The signal can be blocked by a dominant negative mutant of CAML. As shown herein, the TACI protein also can independently activate the AP-1 transcription factor, thus providing both signals required for lymphocyte activation. The TACI protein initiates a novel signal transduction mechanism directly linking cell surface stimuli to the intracellular signaling molecule, CAML, and thereby defines a new class of lymphocyte-specific cell surface receptors that modulate the immune response. In addition, the TACI protein is a novel tool that can be used to regulate the immune system in either a positive or a negative direction. TACI-1 is the human homologue of TACI illustrated in the instant example.

Materials And Methods

Molecular cloning and screening. A human B-lymphocyte cDNA library is screened by the two-hybrid system [Fields & Song, Nature, 340:245–246 (1989)]; [Durfee et al., Genes Dev., 7:555–569 (1993)], with the full coding region of CAML used as bait. The human CAML cDNA is inserted into the yeast two-hybrid bait vector pAS1. This construct directs the expression of a GAL4-DNA binding domain fused to the entire protein sequence of CAML. A B-lymphocyte library in plasmid pACT is transformed into yeast Y153 and potential interacting plasmids are identified by growth of colonies on media lacking histidine and containing 3-amino triazole.

One clone (TACI-1), out of eight primary positives was identified. The TACI-1 cDNA is subcloned into a mammalian expression plasmid which adds an epitope tag to the amino-terminal end of the expressed protein. This construct is then transfected into the Jurkat T-lymphocyte cell line, COS cells, or NIH3T3 cells. In each case, cell surface expression of the TACI protein is demonstrated. The orientation of the protein is with the N-terminus outside the cell, as the epitope is available for reaction with a specific antibody even without permeablizing the cell membrane. This result facilitated the functional studies described herein.

Secondary screening relied on enforced over expression of positive clones in Jurkat T cells, and assaying for NF-AT activation. (Bram et al., 1993, supra) Jurkat T cells transiently transfected with the tagged-TACI-1 construct and an NFAT-reporter plasmid are incubated in medium containing the monoclonal epitope-specific antibody. To maximize cross-linking of TACI1, the antibodies are bound to beads before addition to the cell suspensions. Following a 24 hour incubation, the activity of the NFAT-reporter is determined. A dramatic induction of NFAT reporter activity is found when cells are stimulated in this manner. Control transfections without the TACI-1 construct do not show activation following such treatment. Likewise, transfection of an unrelated cell surface molecule (CD8) followed by anti-CD8 stimulation did not activate NFAT in these cells. The degree of activation was 70–80% of the maximal stimulation that could achieved in these Jurkat T cells by addition of phorbol ester plus ionomycin.

After screening a multiple tissue Northern blot (Clontech) with TACI-1 cDNA (excised from the yeast two-hybrid vector), an independent TACI-1 clone is obtained from a human fetal spleen cDNA library (Stratagene). The 5'-terminal coding region is confirmed by rapid amplification of cDNA ends (RACE) using a 'Marathon-ready' human spleen cDNA library (Clontech), nested TACI-1-specific primers (5'-TCTGAATTGTTTTCAACTTCTC-3' and 5'-CAGCAGAGGATCCCAGTACTGCTC-3'), and Pfu polymerase (Stratagene) according to the manufacturers' recommendations.

Antisera. cDNAs encoding the N-terminal 146 amino acid residues of CAML and the N-terminal 151 residues of TACI-1 are each cloned into a GST-fusion bacterial expression vector (Pharmacia). Rabbit polyclonal antisera are raised against purified GST-fusion proteins [Smith & Johnson, Gene, 67:31–40 (1988)], and specific antibodies are purified by immunoaffinity chromatography over the purified proteins coupled to agarose (Pierce), using standard techniques. Cross-linked anti-TACI-1 is prepared by incubating immunoaffinity-purified polygonal anti-TACI-1 antibodies with anti-rabbit IgG antibody-coupled magnetic beads (PerSeptive Diagnostics).

Screen for Identifying Novel Immunosuppressant Drugs: Jurkat T cells are transfected with TACI-1 expression plasmid and a NF-AT-reporter plasmid. Jurkat T cells naturally express the T-cell receptor (TCR). The cells are stimulated by the addition of antibodies to TACI-1, antibodies to TCR, or antibodies to both. Candidate drugs are mixed with the Jurkat T cells and the effect of these drugs is determined.

The NF-AT-reporter plasmid contains the SEAP reporter. This signal is used to measure the degree of inhibition of activation. The SEAP reporter assay is scaled up so as to be performed by a robot screening apparatus. Drugs that block the activation of TACI-1 but not TCR as measured by the SEAP reporter assay are identified as having selective inhibition of the TACI-1 activated response.

Results and Discussion

Proteins that can interact with CAML are identified by using a two-hybrid screen (Fields & Song, 1989, supra); (Durfee et al., 1993, supra) with CAML as bait. To determine whether one of these identified CAML-binding proteins can affect $Ca^{2+}$ signaling in T-cells, their ability to modulate the activity of the $Ca^{2+}$-dependent transcription factor NF-AT is examined [Truneh et al., Nature, 313:318–321 (1985)]; [Verweij et al., J. Biol. Chem., 265:15788–15795 (1990)]; [Karttunen & Shastri, Proc. Natl. Acad. Sci. USA, 88:3972–3976 (1991)]; [Emmel et al., Science, 246:1617–1620 (1989)]. Enforced over expression of the two-hybrid clones in Jurkat T-cells reveals that one clone (encoding the TACI-1 protein), replaced the requirement for $Ca^{2+}$ influx, implying that TACI-1 lies in the same signal pathway as CAML. Northern blot analysis for TACI-1 mRNA demonstrates a 1.4 kb mRNA expressed only in spleen, small intestine, thymus and peripheral blood lymphocytes suggesting a limited expression of TACI-1 (FIG. 1). The pattern observed is consistent with the expression of TACI-1 being predominantly in peripheral blood cells, since peripheral blood cells, and in particular lymphocytes, can be present in all of these organs (including the Peyer's patches lining the small intestine.) Furthermore, there is no detection of expression in colon, testis, ovary, or prostate. In addition, the TACI-1 protein is detected in all normal peripheral B lymphocytes using specific-antibody staining. There is no detectable protein expressed in peripheral T-lymphocytes, monocytes or neutrophils.

Figure 2C:
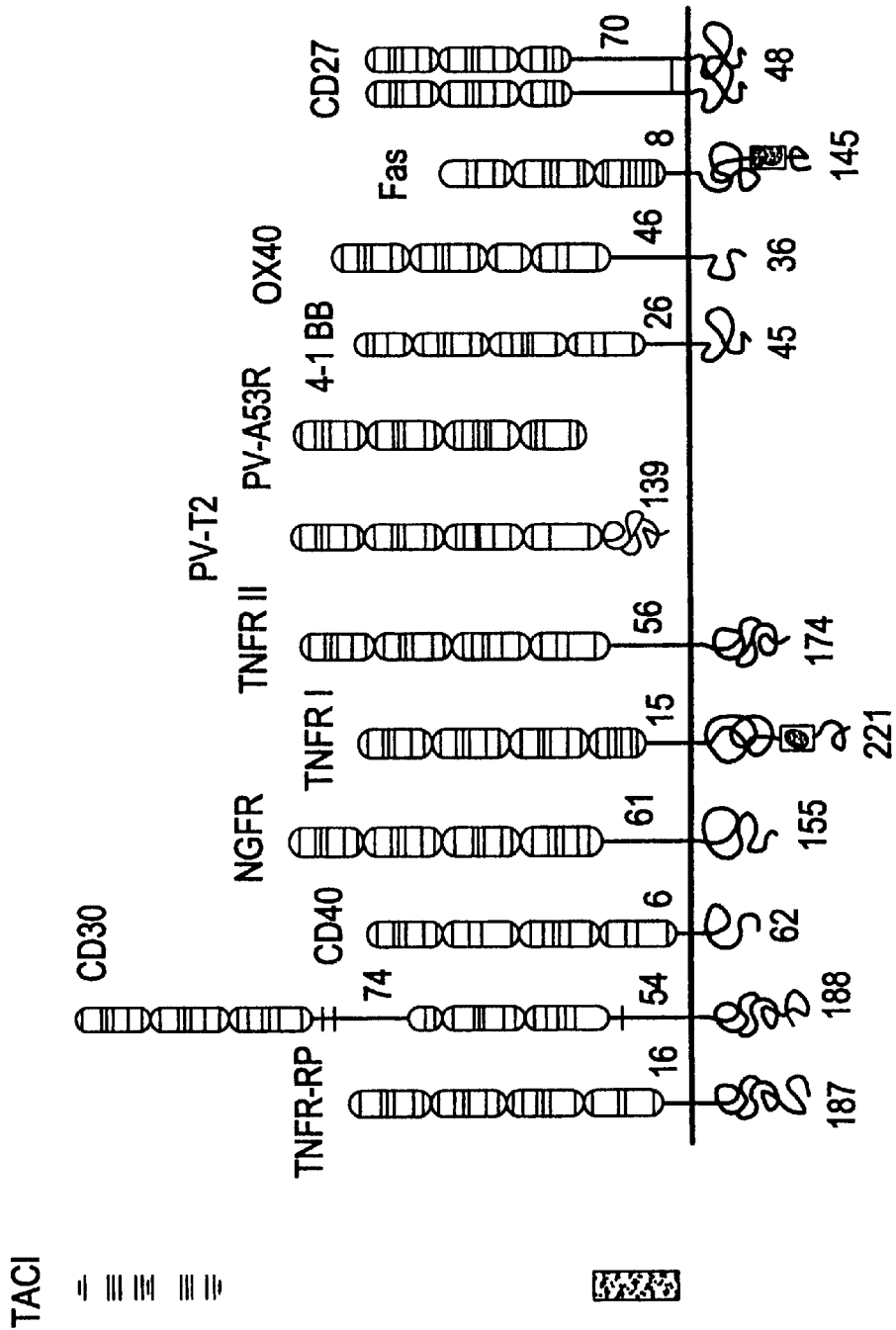
FIG. 2c depicts the cysteine residues of the TACI protein and other TNFR family members.

Determination of the DNA sequence from both strands of the DNA isolated reveals a complete open reading frame of 1325 base pairs, which is predicted to encode a protein of 293 amino acids. The deduced amino acid sequence of TACI-1 (FIG. 2a) includes a single hydrophobic region (residues 167 to 186) that has features of a membrane spanning segment (FIG. 2b). Analysis of the protein sequence by the method of Sipos [Sipos & von Heijne, Eur. J. Biochem., 213:1333–1340 (1993)]; [Claros & von Heijne, Comput. Appl. Biosci., 10:685–686 (1994)], predicts extracellular exposure for the N-terminus and cytoplasmic exposure for the C-terminus. Although TACI-1 lacks an N-terminal signal sequence, the presence of an upstream stop codon indicates that the complete open reading frame is contained within the clone. TACI-1 is relatively rich in cysteine residues, but there is no significant sequence similarity or homology to any other disclosed protein. A search for Prosite motifs in TACI-1 reveals one TNFR_NGFR motif [Bairoch, Nucleic Acids Res., 21:3097–3103 (1993)] (residues 33–71) N-terminal to a putative transmembrane region, which consists of C-x(4,6)-[FYH]-x(5,10)-C-x(0,2)-C-x(2,3)-C-x(7,11)-C-x(4,6)-[DNEQSKP]-SEQ ID NO:11-x(2)-C in the N-terminal half of the protein. This motif is found in a number of proteins, some of which are receptors for growth factors. Some of these proteins have one copy of this motif. A comparison of the TAC-1 protein sequence with itself reveals a significant repeat between the TNFR_NGFR motif at residues 33–66 and residues 70–104. This analysis drew attention to the presence of two TNFR-type cysteine-rich domains encompassing these regions that indicate that TACI-1 is a member of the superfamily of TNFR receptors. (FIG. 2c)

Figure 3A:
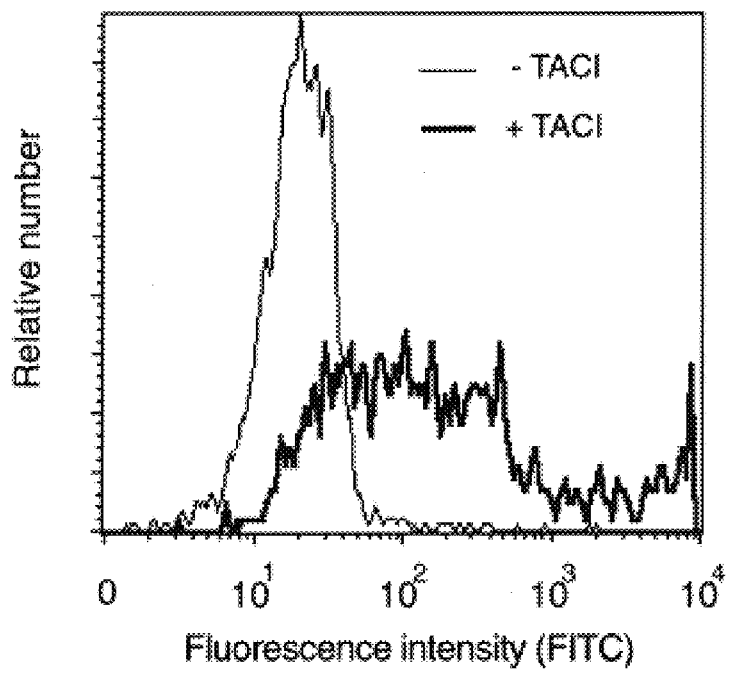
FIG. 3a depicts the flow cytometry of TAg Jurkat T cells transiently transfected with a TACI-1 expression plasmid and the transfection marker, pHook (Invitrogen), or the transfection marker pHook alone. Cell surface expression of TACI-1 and the transfection marker protein, HA-Hook, were detected by indirect immunofluorescence using the immunoaffinity-purified anti-TACI-1 polyclonal antibody and the 12CA5 monoclonal antibody. Depicted data represent TACI-1 staining of cells gated for the transfection marker.
Figure 3B:
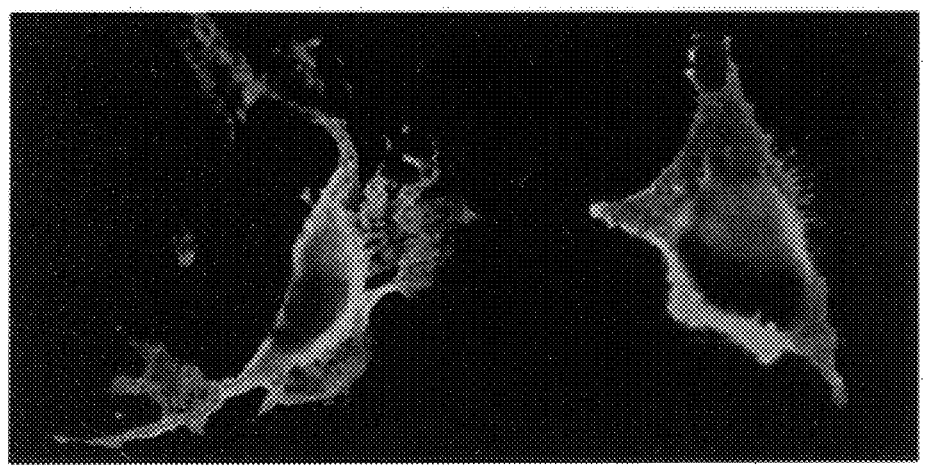
FIG. 3b depicts a photomicrograph showing surface the staining of Cos-7 cells transiently expressing N-terminal FLAG-tagged TACI-1, stained with M2 (anti-FLAG) antibodies and fluorescent anti-mouse IgG antibodies [Bram & Crabtree, Nature, 371:355–358 (1994)]. Surface staining was present whether or not cells were permeabilised with detergent.

To confirm that TACI-1 is a transmembrane protein, its expression on Jurkat T cells transfected with a TACI-1- encoding plasmid using flow cytometry was examined. Cells transfected with TACI-1 show surface staining with rabbit polyclonal antibodies raised against a fusion protein that includes the N-terminal 12 kilodalton portion of TACI-1 (FIG. 3a). Additional evidence that TACI-1 is localized at the cell surface is derived from immunofluorescence microscopy, where surface staining of intact cells transfected with an N-terminal FLAG-epitope-tagged TACI-1 expression plasmid is observed (FIG. 3b). Since the N-terminus of TACI-1 is extracellular in the absence of a cleaved signal sequence, it is a type III transmembrane protein [Wilson-Rawls et al., Virology, 201:66–76 (1994)].

Figure 4A:
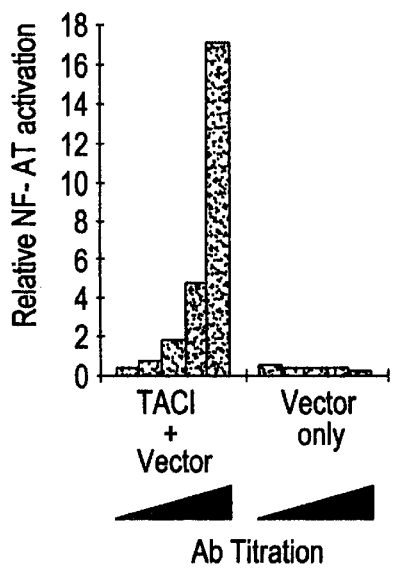
FIG. 4a depicts the activation of an NF-AT-driven secreted alkaline phosphatase reporter. TAg Jurkat T cells, co-transfected with the SXNFAT reporter [Bram et al., Mol. Cell. Biol., 13:4760–4769 (1993)] and the expression plasmid pBJ5 [Takebe, Y., et al., Mol. Cell. Biol., 8:466–472 (1988)] containing either TACI-1-encoding cDNA (solid triangles) or nothing (circles), were treated with 50 ng/ml PMA and the indicated amounts of ionomycin in the presence (closed symbols) and absence (open symbols) of magnetic beads coated with immunoaffinity-purified anti-TACI-1 polyclonal antibodies.
Figure 4B:
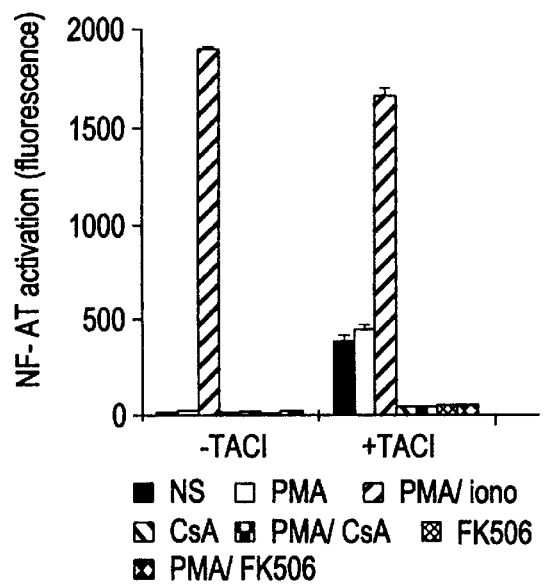
FIG. 4b depicts the activation of NF-AT by antibody-cross linked TACI-1 that is blocked by Cyclosporin A (CsA) or FK506. NF-AT activation was determined in TAg Jurkat T cells co-transfected with SXNFAT and pBJ5 (−TACI-1, left) or pBJ5-TACI-1 (+TACI-1, right), and treated with the indicated combinations of PMA (50 ng/ml), ionomycin (2 µM), CsA (100 ng/ml) and FK506 (500 pg/ml) in the presence of anti-TACI-1 antibody-coated beads ('NS', not stimulated).

To assess the effect of TACI-1 on NF-AT activity in T-cells, the protein is transiently expressed in TAg Jurkat T cells with a secreted alkaline phosphatase reporter driven by the NF-AT-binding sequences from the IL-2 promoter (Bram & Crabtree, 1994, supra); [Fiering et al., Genes Dev., 4:1823–1834 (1990)]; (Bram et al., 1993, supra). TACI-1 over expression can partially replace the requirement for ionomycin in this assay. The addition of anti-TACI-1 antibodies to the cells further increased NF-AT activation (more than twofold, see FIG. 4a), demonstrating that TACI-1 responds to cross-linking at the cell surface. The degree of NF-AT activation varies in different experiments due to transfection efficiency but is typically 40–50% of the maximal response to the corresponding treatment of the cells with PMA plus ionomycin. TACI-1-mediated NF-AT activation is dependent on calcineurin, as is demonstrated by the loss of NF-AT activity in the presence of an immunosuppressive drugs, such as Cyclosporin A or FK506 [Friedman & Weissman, Cell, 66:799–806 (1991)]; (Lui et al., 1991, supra) (FIG. 4b).

Figure 4C:
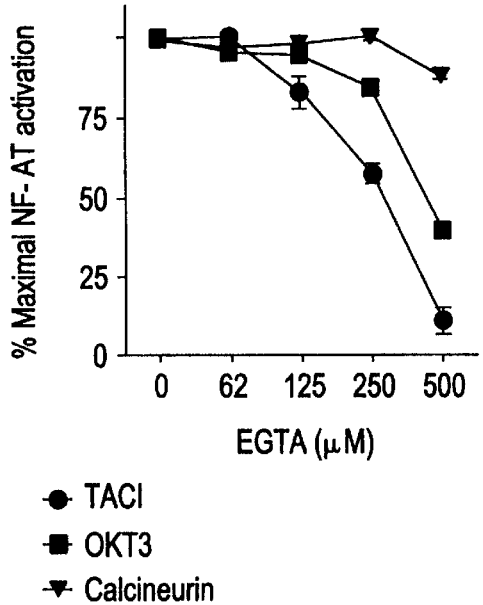
FIG. 4c shows that NF-AT activation by antibody-cross linked TACI-1 requires extracellular calcium. NF-AT activation was measured in the presence of EGTA in Jurkat T cells over expressing TACI-1. The treatments included cross linked anti-TACI-1 (circles), transfection with a C-terminally truncated, calcium-independent calcineurin A subunit (triangles), or activation with the TCR stimulating antibody OKT3 (squares). All cells were co-stimulated by the addition of PMA to 50 ng/ml.

To examine the requirement for $Ca^{2+}$ influx in TACI-1-mediated activation of NF-AT, extracellular calcium can be removed by the addition of increasing concentrations of EGTA. This results in the inhibition of TACI-1-mediated NF-AT activation, as has been shown previously for T-cell receptor-mediated activation (FIG. 4c). As a control, the effect of expressing in the cells, a constitutively active, calcium-independent mutant of calcineurin A [Hubbard & Klee, Biochemistry, 28:1868–74 (1989)]; (O'Keefe et al., 1992, supra); (Clipstone & Crabtree, 1993, supra) is examined. As expected, in these cells NF-AT activation is seen even in the presence of EGTA (FIG. 4c). Thus, in T-cells, TACI-1 mediates the calcineurin-dependent aspect of the activation of NF-AT by initiating the influx of extracellular $Ca^{2+}$ (most likely through the capacitative $Ca^{2+}$ influx pathway following the depletion of intracellular stores [Putney & Bird, Cell, 75:199–201 (1993)]; Hoth & Prenner, Physiol., 465:359–386 (1993)]; [Zweifach & Lewis, Proc. Natl. Acad. Sci. USA, 90:6295–6299 (1993)]; [Premack et al., J. Immunol., 152:5226–5240 (1994)]).

Figure 4D:
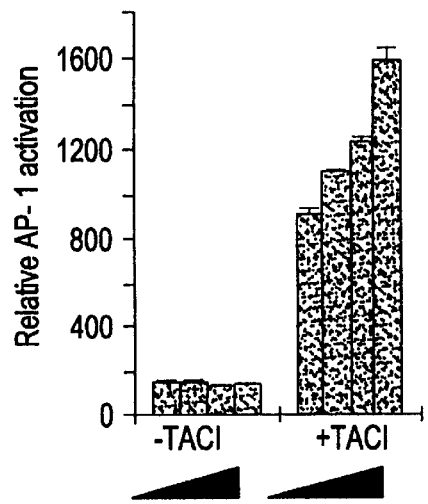
FIG. 4d depicts the activation of an AP-1-driven secreted alkaline phosphatase reporter. AP-1 activation was measured in TAg Jurkat T cells, co-transfected with a mouse metallothionein AP-1-SEAP reporter [Bram et al., 1991, supra] and pBJ5 containing no insert (−TACI-1, left) or TACI-1 cDNA (+TACI-1, right). Cells were incubated in the absence, and with serially increasing amounts, of cross linked anti-TACI-1 antibodies. To control for transfection efficiency, a plasmid containing a constitutive promoter driving the expression of luciferase (EF-Luc) was included.

Activation of NF-AT by CAML requires exogenous stimulation of protein kinase C by the addition of phorbol ester (Bram & Crabtree, 1994, supra). Antibody-cross linked TACI-1, however, is able to activate NF-AT in the absence of either PMA or ionomycin (FIG. 4b, solid bars). Experiments examining the activation of an AP-1 reporter by the over expression of TACI-1 shows that AP-1 activation is elevated (over four-fold) in TACI-1-transfected Jurkat T cells. This effect can be further enhanced with the addition of cross-linked anti-TACI-1 antibodies (FIG. 4d). Therefore, TACI-1 initiates $Ca^{2+}$ influx, which in turns activates calcineurin, as well as activates the AP-1 pathway following stimulation, thereby mediating the fulfillment of both requirements for the activation of NF-AT.

Figures 5A, 5D:
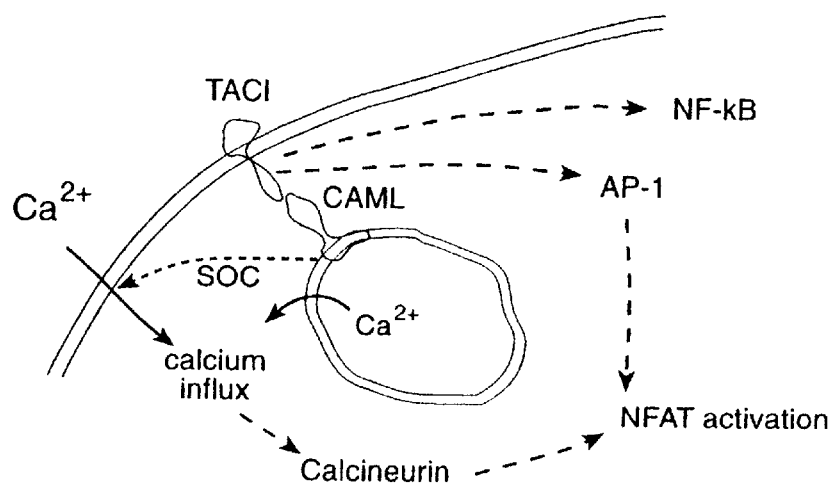
FIG. 5a shows the yeast 2-hybrid interaction. Full-length cDNAs and indicated deletion mutants of TACI-1 and CAML were cloned into the yeast expression plasmids pACT and/or pAS1, and the indicated combinations were tested for interaction with the yeast 2-hybrid system ('+', positive interaction; '−', no interaction; 'ND', not done).
FIG. 5d depicts a schematic diagram showing the TACI-1/CAML signal transduction model ('SOC', stores-operated calcium channel).
Figure 5B:
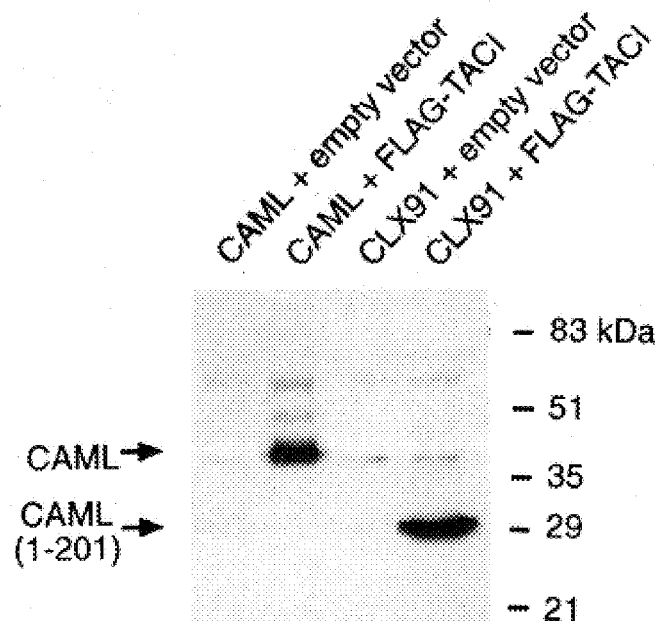
FIG. 5b depicts the co-immunoprecipitation of CAML with TACI-1. 293T cells were transfected with the indicated combinations of the expression plasmid pBJ5 containing cDNAs for CAML, TACI-1 with an N-terminal FLAG tag, the N-terminal 146 amino acids of CAML (CLX91), or no insert. After incubation for 48 hours, the cells were lysed (1% dodecyl maltoside, 20 mM HEPES pH 7.4, 150 mM NaCl, 10% glycerol, 2 mM $MgSO_4$, 1 mM $CaCl_2$, 1 mM PMSF) and the lysate was clarified by centrifugation. FLAG-tagged TACI-1 and associated proteins were immunoprecipitated with anti-FLAG monoclonal antibody-conjugated agarose beads and subjected to Western transfer using standard protocols. The Western blot was probed with immunoaffinity-purified anti-CAML polyclonal antibodies followed by chemiluminescent detection (Amersham). Parallel Western blots, performed for each sample, confirmed the expected expression of TACI-1, CAML or the truncated CAML mutant in all transfections.

Further confirmation that TACI-1 interacts with CAML can be demonstrated by their specific interaction in a two-hybrid reverse swap experiment (Durfee et al., 1993, supra) (FIG. 5a). To define the critical amino acid residues involved in the interaction, deletion mutants of both TACI-1 and CAML are tested for their ability to physically associate (FIG. 5a). The C-terminal 126 amino acids of TACI-1 are found to be sufficient for binding to the N-terminal 146 amino acids of CAML. Additional evidence for the in vivo association of TACI-1 with CAML is provided by experiments in which full length CAML and a mutant comprising the 146 N-terminal amino acid residues of CAML are co-immunoprecipitated with TACI-1 from cell lysates (FIG. 5b). Therefore, it may be concluded that the cytoplasmic C-terminal tail of TACI-1 can physically associate with the N-terminal half of CAML.

Figure 5C:
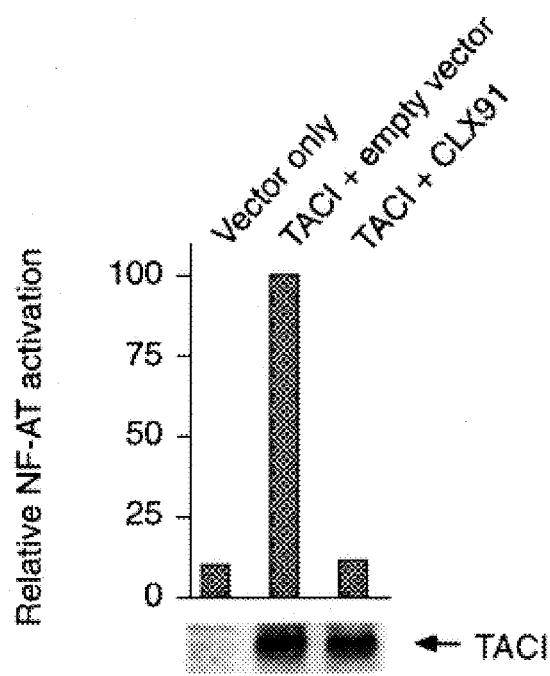
FIG. 5c shows that the over expression of the N-terminal half of CAML has a dominant negative effect on TACI-1-induced NF-AT activation. NF-AT activation was determined in TAg Jurkat cells transfected with pBJ5 alone, pBJ5-TACI-1 plus the control plasmid, or pBJ5-TACI-1 with an equivalent amount of CLX91, following treatment with TACI-1-specific antibodies (top). TACI-1 expression in these transfections was determined by Western blot using anti-TACI-1 polyclonal antibodies (bottom).

To examine whether TACI-1 signaling depends on the association of TACI-1 with CAML, the interacting domain of CAML (residues 1–146) is tested to determine if it can inhibit TACI-1-induced NF-AT activation in a dominant negative fashion. Co-transfection of the mutant CAML (1–146) expression plasmid completely eliminates TACI-1-induced NF-AT activation in Jurkat T cells. On the other hand, there is no inhibitory effect on PMA plus ionomycin-induced NF-AT activity, thus ruling out a nonspecific toxic effect. Co-expression of CAML(1–146) also does not influence the accumulation of TACI-1 protein as detected by Western blot analysis (FIG. 5c). CAML(1–146) lacks the hydrophobic transmembrane domains that are required for $Ca^{2+}$ influx activity [Holloway & Bram, Biol. Chem., 271:8549–8552 (1996)]. Hence the elimination of NF-AT-inducing activity in these cells can be attributed to binding of the CAML(1–146) fragment to the intracellular C-terminal portion of TACI-1, preventing association with endogenous full-length CAML.

CAML is an integral membrane protein localized to cytoplasmic vesicles (Bram & Crabtree, 1994, supra). Analysis of deletion mutants has shown that hydrophobic domains in the C-terminal half of the protein are essential for activity (Holloway & Bram, 1996, supra), and that the hydrophilic N-terminal half of the protein may have a regulatory role. Trypsin digestion experiments further demonstrated that the N-terminal half of the molecule is cytoplasmic. Here, the interaction between TACI-1 and CAML is required for TACI-1-mediated NF-AT activation in Jurkat T cells is demonstrated. Taken together, these data indicate that a physical interaction between TACI-1 in the plasma membrane and intracellular CAML-containing vesicles can initiate a calcium influx signal (FIG. 5d). These findings provide the first evidence for direct communication between cell surface receptors and intracellular organelles in lymphocytes. This mechanism may be somewhat analogous to the dihydropyridine-ryanodine receptor model in muscle cells, in which stimulation of one molecule can directly modulate the activity of the other [Marty et al., Proc. Natl. Acad. Sci. USA, 91:2270–2274 (1994)]; [Sham et al., Proc. Natl. Acad. Sci. USA, 92:121–125 (1995)]; [Nakai et al., Nature, 380:72–75 (1996)].

Other cell surface proteins have been shown to activate lymphocyte function, including the CD3 T-cell receptor, CD2, CD20, and Thy-1. These proteins have no sequence-homology with TACI-1, and it is likely that they play different roles from each other, either in terms of response to different extracellular signals, and/or in terms of developmental stage of expression on lymphocytes. TACI-1 must also play a role in the modulation of the function of lymphocytes in alternate and/or co-stimulatory pathways. Thus, in addition to defining a new signaling mechanism, TACI-1 is a novel lymphocyte-specific receptor capable of activating T-cells.

The following is a list of documents related to the above disclosure and particularly to the experimental procedures and discussions. These documents, and all others cited above, should be considered as incorporated by reference in their entirety.
1. Imboden, J. B., Weiss, A. & Stobo, J. D., *J. Immunol.,* 134:663–5 (1985).
2. Crabtree, G. R. & Clipstone, N. A., *Annu. Rev. Biochem.,* 63:1045–83 (1994).
3. Weiss, A. & Littman, D. R., *Cell,* 76:263–74 (1994).
4. Bram, R. J. & Crabtree, G. R., *Nature,* 371:355–8 (1994).
5. Fields, S. & Song, O., *Nature,* 340:245–6 (1989).
6. Durfee, T., et al., *Genes Dev.,* 7:555–69 (1993).
7. Truneh, A., Albert, F., Golstein, P. & Schmitt, V. A., *Nature,* 313:318–21 (1985).
8. Verweij, C. L., Guidos, C. & Crabtree, G. R., *J. Biol. Chem.,* 265:15788–95 (1990).
9. Karttunen, J. & Shastri, N., *Proc. Natl. Acad. Sci. USA,* 88:3972–6 (1991).
10. Sipos, L. & von Heijne, G., *Eur. J. Biochem.,* 213:1333–40 (1993).
11. Claros, M. G. & von Heijne, G. *Comput. Appl. Biosci.,* 10:685–6 (1994).
12. Bairoch, A., *Nucleic Acids Res.,* 21:3097–103 (1993).
13. Wilson-Rawls, J., Deutscher, S. L. & Wold, W. S., *Virology,* 201:66–76 (1994).
14. Fiering, S., et al., *Genes Dev.,* 4:1823–34 (1990).
15. Bram, R. J., Hung, D. T., Martin, P. K., Schreiber, S. L. & Crabtree, G. R., *Mol. Cell. Biol.,* 13:4760–9 (1993).
16. Friedman, J. & Weissman, I., *Cell,* 66:799–806 (1991).
17. Liu, J., et al., *Cell,* 66:807–15 (1991).
18. Hubbard, M. J. & Klee, C. B., *Biochemistry,* 28:1868–74 (1989).
19. O'Keefe, S. J., Tamura, J., Kincaid, R. L., Tocci, M. J. & O'Neill, E. A., *Nature,* 357:692–4 (1992).
20. Clipstone, N. A. & Crabtree, G. R., *Ann. N.Y. Acad. Sci.,* 696:20–30 (1993).
21. Putney, J. W., Jr. & Bird, G. S., *Cell,* 75:199–201 (1993).
22. Hoth, M. & Prenner, R., *J. Physiol. (Lond.),* 465:359–86 (1993).
23. Zweifach, A. & Lewis, R. S., *Proc. Natl. Acad. Sci. USA,* 90:6295–9 (1993).
24. Premack, B. A., McDonald, T. V. & Gardner, P., *J. Immunol.,* 152:5226–40 (1994).
25. Holloway, M. P. & Bram, R. J., *J. Biol. Chem.,* 271:8549–52 (1996).
26. Marty, I., et al., *Proc. Natl. Acad. Sci. USA,* 91:2270–4 (1994).
27. Sham, J. S., Cleemann, L. & Morad, M., *Proc. Natl. Acad. Sci. USA,* 92:121–5 (1995).
28. Nakai, J., et al., *Nature,* 380:72–5 (1996).
29. Smith, D. B. & Johnson, K. S., *Gene,* 67:31–40 (1988).
30. Takebe, Y., et al., *Mol. Cell. Biol.,* 8:466–72 (1988).
31. Emmel et al., *Science,* 246:1617–1620 (1989).
32. Mattila et al., *Emble J,* 9:4425–33 (1990).

Various publications in addition to the immediately foregoing are cited herein, the disclosures of which are incorporated by reference in their entireties. The citation of any reference herein should not be deemed as an admission that such reference is available as prior art to the instant invention.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

What is claimed is:

1. An isolated Transmembrane Activator and CAML Interactor (TACI) protein that functions as a cell surface signaling protein comprising an extracellular domain, a membrane spanning segment, and a cytoplasmic domain that has a binding affinity for CAML, wherein said TACI protein is a plasma membrane receptor that interacts directly with an intracellular organelle in lymphocytes.

2. The TACI protein of claim 1 that has the characteristic of comprising a monomer which consists of about 295 amino acids.

3. The TACI protein of claim 1 that has the characteristics of comprising:
    (a) a monomer that consists of about 295 amino acids; and
    (b) two TNFR_NGFR motifs, wherein each TNFR_NGFR motif has the amino acid sequence of SEQ ID NO:11.

4. The TACI protein of claim 1 that has an amino acid sequence comprising SEQ ID NO:2.

5. The TACI protein of claim 1 that has an amino acid sequence comprising SEQ ID NO:2 having at least one conservative amino acid substitution.

6. An isolated polypeptide encoded by a nucleic acid consisting of at least 18 consecutive nucleotides of a nucleotide sequence, wherein said nucleotide sequence encodes a Transmembrane Activator and CAML Interactor (TACI) protein having the amino acid sequence of SEQ ID NO:2; wherein the polypeptide functions as a cell surface signaling protein comprising an extracellular domain, a membrane spanning segment, and a cytoplasmic domain that has a binding affinity for CAML; and wherein said TACI protein is a plasma membrane receptor that interacts directly with an intracellular organelle in lymphocytes.

7. A proteolytic fragment of an isolated Transmembrane Activator and CAML Interactor (TACI) protein; wherein said TACI protein functions as a cell surface signaling protein comprising an extracellular domain, a membrane spanning segment, and a cytoplasmic domain that has a binding affinity for CAML, an wherein said TACI protein is a plasma membrane receptor that interacts directly with an intracellular organelle in lymphocytes.

8. The proteolytic fragment of claim 7 wherein the TACI protein further has the characteristics of comprising:

(a) a monomer that consists of about 295 amino acids; and (b) two TNFR_NGFR motifs, wherein each TNFR_NGFR motif has the amino acid sequence of SEQ ID NO:11.

9. The proteolytic fragment of claim 7, wherein the TACI protein has the amino acid sequence of SEQ ID NO:2.

10. An isolated polypeptide comprising an N-terminal fragment of a Transmembrane Activator and CAML Interactor (TACI) protein; wherein said TACI protein functions as a cell surface signaling protein comprising an extracellular domain, a membrane spanning segment, and a cytoplasmic domain that has a binding affinity for CAML, wherein said TACI protein is a plasma membrane receptor that interacts directly with an intracellular organelle in lymphocytes; and wherein said N-terminal fragment corresponds to the regulatory extracellular domain of the TACI.

11. The isolated polypeptide of claim 10 comprising the amino acid sequence of SEQ ID NO:6.

12. The isolated polypeptide of claim 10 comprising the amino acid sequence of SEQ ID NO:6 having at least one conservative amino acid substitution.

13. A chimeric protein comprising the polypeptide of claim 10.

14. The chimeric protein of claim 13 wherein the polypeptide comprises the amino acid sequence of SEQ ID NO:6.

15. The chimeric protein of claim 13 wherein the polypeptide comprises the amino acid sequence of SEQ ID NO:6 having at least one conservative amino acid substitution.

16. An isolated polypeptide comprising a C-terminal fragment of a Transmembrane Activator and CAML Interactor (TACI) protein; wherein said TACI protein functions as a cell surface signaling protein comprising an extracellular domain, a membrane spanning segment, and a cytoplasmic domain that has a binding affinity for CAML, wherein said TACI protein is a plasma membrane receptor that interacts directly with an intracellular organelle in lymphocytes; and wherein said C-terminal fragment is sufficient to bind the N-terminal 146 amino acids of CAML.

17. The isolated polypeptide of claim 16, wherein said C-terminal fragment comprises about 126 amino acids of the C-terminus of the TACI protein.

18. The isolated polypeptide of claim 16, wherein said C-terminal fragment comprises the amino acid sequence of SEQ ID NO:4.

19. The isolated polypeptide of claim 16 comprising the amino acid sequence of SEQ ID NO:4 having at least one conservative amino acid substitution.

20. A chimeric protein comprising the polypeptide of claim 16.

21. The chimeric protein of claim 20 wherein the polypeptide comprises the amino acid sequence of SEQ ID NO:4.

22. The chimeric protein of claim 20 wherein the polypeptide comprises the amino acid sequence of SEQ ID NO:4 having at least one conservative amino acid substitution.

23. The TACI protein of claim 1 that comprises a TNFR_NGFR motif, wherein said TNFR_NGFR motif has the amino acid sequence of SEQ ID NO:11.

24. The TACI protein of claim 23 that further comprises a second TNFR_NGFR motif, wherein said second TNFR_NGFR motif has the amino acid sequence of SEQ ID NO:11.

* * * * *

UNITED STATES PATENT AND TRADEMARK OFFICE
CERTIFICATE OF CORRECTION

PATENT NO. : 5,969,102
DATED : October 19, 1999
INVENTOR(S) : Richard J. Bram and Gotz Von Bulow It is certified that error appears in the above-identified patent and that said Letters Patent is hereby corrected as shown below:

In the Sequence Listing, Column 57, under (2) INFORMATION FOR SEQ NO:11 and (ii) MOLECULE TYPE: peptide, the (A) DESCRIPTION should read as:
-- (A) DESCRIPTION: Xaa at Positions 2-7 may be 1 or 2 residues less; Xaa at Positions 8 may be Phe, Tyr, or His; Xaa at Positions 9-18 may be 1-5 residues less; Xaa at Positions 20, 21 may be 1 or 2 residues less; Xaa at Positions 23-25 may be 1 residue less; Xaa at Positions 27-37 may be 1-4 residues less; Xaa at Positions 39-44 may be 1 or 2 residues less; Xaa at Positions 45 may be Asp, Asn, Glu, Ser, Lys, or Pro. --

Signed and Sealed this

First Day of May, 2001

Attest:

NICHOLAS P. GODICI

*Attesting Officer*    *Acting Director of the United States Patent and Trademark Office*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1377 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (vi) ORIGINAL SOURCE:
      (A) ORGANISM: Homo sapiens (xi) SEQUENCE DESCRIPTION: SEQ ID NO:1:

```
AGCATCCTGA GTAATGAGTG GCCTGGGCCG GAGCAGGCGA GGTGGCCGGA GCCGTGTGGA      60

CCAGGAGGAG CGCTTTCCAC AGGGCCTGTG GACGGGGGTG GCTATGAGAT CCTGCCCCGA     120

AGAGCAGTAC TGGGATCCTC TGCTGGGTAC CTGCATGTCC TGCAAAACCA TTTGCAACCA     180

TCAGAGCCAG CGCACCTGTG CAGCCTTCTG CAGGTCACTC AGCTGCCGCA AGGAGCAAGG     240
```

```
CAAGTTCTAT GACCATCTCC TGAGGGACTG CATCAGCTGT GCCTCCATCT GTGGACAGCA      300

CCCTAAGCAA TGTGCATACT TCTGTGAGAA CAAGCTCAGG AGCCCAGTGA ACCTTCCACC      360

AGAGCTCAGG AGACAGCGGA GTGGAGAAGT TGAAAACAAT TCAGCAACT CGGGAAGGTA       420

CCAAGGATTG GAGCACAGAG GCTCAGAAGC AAGTCCAGCT CTCCCGGGGC TGAAGCTGAG      480

TGCAGATCAG GTGGCCCTGG TCTACAGCAC GCTGGGGCTC TGCCTGTGTG CCGTCCTCTG      540

CTGCTTCCTG GTGGCGGTGG CCTGCTTCCT CAAGAAGAGG GGGGATCCCT GCTCCTGCCA      600

GCCCCGCTCA AGGCCCCGTC AAAGTCCGGC CAAGTCTTCC CAGGATCACG CGATGGAAGC      660

CGGCAGCCCT GTGAGCACAT CCCCCGAGCC AGTGGAGACC TGCAGCTTCT GCTTCCCTGA      720

GTGCAGGGCG CCCACGCAGG AGAGCGCAGT CACGCCTGGG ACCCCCGACC CCACTTGTGC      780

TGGAAGGTGG GGGTGCCACA CCAGGACCAC AGTCCTGCAG CCTTGCCCAC ACATCCCAGA      840

CAGTGGCCTT GGCATTGTGT GTGTGCCTGC CCAGGAGGGG GGCCCAGGTG CATAAATGGG      900

GGTCAGGGAG GGAAAGGAGG AGGGAGAGAG ATGGAGAGGA GGGGAGAGAG AAAGAGAGGT      960

GGGGAGAGGG GAGAGAGATA TGAGGAGAGA GAGACAGAGG AGGCAGAAAG GGAGAGAAAC     1020

AGAGGAGACA GAGAGGGAGA GAGAGACAGA GGGAGAGAGA GACAGAGGGG AAGAGAGGCA     1080

GAGAGGGAAA GAGGCAGAGA AGGAAAGAGA CAGGCAGAGA AGGAGAGAGG CAGAGAGGGA     1140

GAGAGGCAGA GAGGGAGAGA GGCAGAGAGA CAGAGAGGGA GAGAGGGACA GAGAGAGATA     1200

GAGCAGGAGG TCGGGGCACT CTGAGTCCCA GTTCCCAGTG CAGCTGTAGG TCGTCATCAC     1260

CTAACCACAC GTGCAATAAA GTCCTCGTGC CTGCTGCTCA CAGCCCCCGA GAGCCCCTCC     1320

TCCTGGAGAA TAAAACCTTT GGCAGCTGCC CTTCCTCAAA AAAAAAAAAA AAAAAAA       1377
```

(2) INFORMATION FOR SEQ ID NO:2:

(i) SEQUENCE CHARACTERISTICS:
        (A) LENGTH: 293 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (vi) ORIGINAL SOURCE:
        (A) ORGANISM: Homo sapiens (xi) SEQUENCE DESCRIPTION: SEQ ID NO:2:

```
Met Ser Gly Leu Gly Arg Ser Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110
```

-continued

```
Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
                180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
        210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
                260                 265                 270

His Ile Pro Asp Ser Gly Leu Gly Ile Val Cys Val Pro Ala Gln Glu
        275                 280                 285

Gly Gly Pro Gly Ala
    290
```

(2) INFORMATION FOR SEQ ID NO:3:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:3:

```
AAGAAGAGGG GGGATCCCTG CTCCTGCCAG CCCCGCTCAA GGCCCCGTCA AAGTCCGGCC      60
AAGTCTTCCC AGGATCACGC GATGGAAGCC GGCAGCCCTG TGAGCACATC CCCCGAGCCA     120
GTGGAGACCT GCAGCTTCTG CTTCCCTGAG TGCAGGGCGC CCACGCAGGA GAGCGCAGTC     180
ACGCCTGGGA CCCCCGACCC CACTTGTGCT GGAAGGTGGG GGTGCCACAC CAGGACCACA     240
GTCCTGCAGC CTTGCCCACA CATCCCAGAC AGTGGCCTTG GCATTGTGTG TGTGCCTGCC     300
CAGGAGGGGG GCCCAGGTGC A                                               321
```

(2) INFORMATION FOR SEQ ID NO:4:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: C-terminal (vi) ORIGINAL SOURCE:
    (A) ORGANISM: Homo sapiens (xi) SEQUENCE DESCRIPTION: SEQ ID NO:4:

```
Lys Lys Arg Gly Asp Pro Cys Ser Cys Gln Pro Arg Ser Arg Pro Arg
1               5                   10                  15

Gln Ser Pro Ala Lys Ser Ser Gln Asp His Ala Met Glu Ala Gly Ser
            20                  25                  30

Pro Val Ser Thr Ser Pro Glu Pro Val Glu Thr Cys Ser Phe Cys Phe
                35                  40                  45

Pro Glu Cys Arg Ala Pro Thr Gln Glu Ser Ala Val Thr Pro Gly Thr
        50                  55                  60

Pro Asp Pro Thr Cys Ala Gly Arg Trp Gly Cys His Thr Arg Thr Thr
65                  70                  75                  80

Val Leu Gln Pro Cys Pro His Ile Pro Asp Ser Gly Leu Gly Ile Val
                85                  90                  95

Cys Val Pro Ala Gln Glu Gly Gly Pro Gly Ala
            100                 105
```

(2) INFORMATION FOR SEQ ID NO:5:

(i) SEQUENCE CHARACTERISTICS:
       (A) LENGTH: 498 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (vi) ORIGINAL SOURCE:
       (A) ORGANISM: Homo sapiens (xi) SEQUENCE DESCRIPTION: SEQ ID NO:5:

```
ATGAGTGGCC TGGGCCGGAG CAGGCGAGGT GGCCGGAGCC GTGTGGACCA GGAGGAGCGC    60
TTTCCACAGG GCCTGTGGAC GGGGGTGGCT ATGAGATCCT GCCCCGAAGA GCAGTACTGG   120
GATCCTCTGC TGGGTACCTG CATGTCCTGC AAAACCATTT GCAACCATCA GAGCCAGCGC   180
ACCTGTGCAG CCTTCTGCAG GTCACTCAGC TGCCGCAAGG AGCAAGGCAA GTTCTATGAC   240
CATCTCCTGA GGGACTGCAT CAGCTGTGCC TCCATCTGTG ACAGCACCC TAAGCAATGT    300
GCATACTTCT GTGAGAACAA GCTCAGGAGC CCAGTGAACC TTCCACCAGA GCTCAGGAGA   360
CAGCGGAGTG GAGAAGTTGA AAACAATTCA GACAACTCGG GAAGGTACCA AGGATTGGAG   420
CACAGAGGCT CAGAAGCAAG TCCAGCTCTC CCGGGGCTGA AGCTGAGTGC AGATCAGGTG   480
GCCCTGGTCT ACAGCACG                                                 498
```

(2) INFORMATION FOR SEQ ID NO:6:

(i) SEQUENCE CHARACTERISTICS:
       (A) LENGTH: 166 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: N-terminal (vi) ORIGINAL SOURCE:
       (A) ORGANISM: Homo sapiens (xi) SEQUENCE DESCRIPTION: SEQ ID NO:6:

Met Ser Gly Leu Gly Arg Ser Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
            50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
                    100                 105                 110

Asn Leu Pro Pro Glu Leu Arg Arg Gln Arg Ser Gly Glu Val Glu Asn
            115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr
                165

(2) INFORMATION FOR SEQ ID NO:7:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:7:

CTGGGGCTCT GCCTGTGTGC CGTCCTCTGC TGCTTCCTGG TGGCGGTGGC CTGCTTCCTC    60

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens (xi) SEQUENCE DESCRIPTION: SEQ ID NO:8:

-continued

```
Leu Gly Leu Cys Leu Cys Ala Val Leu Cys Cys Phe Leu Val Ala Val
1               5                   10                  15

Ala Cys Phe Leu
            20
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:9:

TCTGAATTGT TTTCAACTTC TC                        22

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:10:

CAGCAGAGGA TCCCAGTACT GCTC                    24

(2) INFORMATION FOR SEQ ID NO:11:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide
        (A) DESCRIPTION: Xaa at Positions 2-7 may be 1 or 2
            residues less; Xaa at Positi (iii) HYPOTHETICAL: NO (xi) SEQUENCE DESCRIPTION: SEQ ID NO:11:

```
Cys Xaa Xaa Xaa Xaa Xaa Xaa Xaa Xaa Xaa Xaa Xaa Xaa Xaa Xaa Xaa
1               5                   10                  15

Xaa Xaa Cys Xaa Xaa Cys Xaa Xaa Xaa Cys Xaa Xaa Xaa Xaa Xaa Xaa
            20                  25                  30

Xaa Xaa Xaa Xaa Xaa Cys Xaa Xaa Xaa Xaa Xaa Xaa Xaa Xaa Xaa Cys
        35                  40                  45
```